: 
United States Patent [19]

Bouma et al.

[11] Patent Number: 5,484,699
[45] Date of Patent: Jan. 16, 1996

[54] NUCLEOTIDE SEQUENCES USEFUL AS TYPE SPECIFIC PROBES, PCR PRIMERS AND LCR PROBES FOR THE AMPLIFICATION AND DETECTION OF HUMAN PAPILLOMA VIRUS, AND RELATED KITS AND METHODS

[75] Inventors: Stanley R. Bouma, Mundelein, Ill.; Jeffrey L. Joseph, Cherry Hill, N.J.; Ronald L. Marshall, Zion; Thomas G. Laffler, Libertyville, both of Ill.

[73] Assignee: Abbott Laboratories, Abbott Park, Ill.

[21] Appl. No.: 316,293

[22] Filed: Sep. 30, 1994

Related U.S. Application Data

[63] Continuation of Ser. No. 965,665, Oct. 22, 1992, abandoned, which is a continuation-in-part of Ser. No. 589,948, Sep. 28, 1990, abandoned, and a continuation-in-part of Ser. No. 590,105, Sep. 28, 1990, abandoned, and a continuation-in-part of Ser. No. 590,253, Sep. 28, 1990, abandoned.

[51] Int. Cl.$^6$ .............................. C12Q 1/70; C07H 21/02; C07H 21/04
[52] U.S. Cl. ..................... 435/5; 536/23.1; 536/23.72
[58] Field of Search .......................... 435/5, 6; 935/77, 935/78; 536/23.1, 23.72, 24.3

[56] References Cited

U.S. PATENT DOCUMENTS

| | | | |
|---|---|---|---|
| 4,849,331 | 7/1989 | Lorinez | 435/5 |
| 4,849,332 | 7/1989 | Lorinez | 435/5 |
| 4,849,334 | 7/1989 | Lorinez | 435/5 |
| 4,908,306 | 3/1990 | Lorinez | 435/5 |
| 5,182,377 | 1/1993 | Manos et al. | 536/24.32 |

FOREIGN PATENT DOCUMENTS 8803957   6/1988   WIPO .

OTHER PUBLICATIONS

Seedort et al., Virology 145: 181–185 (1985) "Human Papillomavirus Type 16 DNA Sequence".

Primary Examiner—W. Gary Jones
Assistant Examiner—Eggerton Campbell
Attorney, Agent, or Firm—Paul D. Yasger; Thomas D. Brainard

[57] ABSTRACT

Short nucleotide sequences of human papilloma virus useful for the determination of the presence and type of human papilloma virus present in a test sample. The sequences provided can be amplified by polymerase chain reaction or ligase chain reaction. The sequences provided also can be hybridized by standard slot-, dot- or replica-blot procedures. Methods and kits also are provided for the detection of human papilloma virus in a test sample and the determination of the type of human papilloma virus present in the test sample.

2 Claims, 6 Drawing Sheets

SEQUENCE LISTING ( 1 ) GENERAL INFORMATION:

( i i i ) NUMBER OF SEQUENCES: 96

( 2 ) INFORMATION FOR SEQ ID NO: 1:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 1:

CAGATGTCTC TGTGGCGGCC TAGTG                    25

( 2 ) INFORMATION FOR SEQ ID NO: 2:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 2:

CGTTTTCCAT ATTTTTTGC AGATG                    25

( 2 ) INFORMATION FOR SEQ ID NO: 3:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 3:

AAGTTGTAAG CACCGATGAA TATGT                    25

( 2 ) INFORMATION FOR SEQ ID NO: 4:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 4:

AATGTACCCT AAATACCCTA TATTG                    25

( 2 ) INFORMATION FOR SEQ ID NO: 5:

( i ) SEQUENCE CHARACTERISTICS:

```
            ( A ) LENGTH: 25
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 5:
```

AGGTGTCAGG AAAACCAAAT TTATT                                              25

```
( 2 ) INFORMATION FOR SEQ ID NO: 6:

( i ) SEQUENCE CHARACTERISTICS:
            ( A ) LENGTH: 23
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 6:
```

GAATTAGTTA GACCATTTAA AAG                                                23

```
( 2 ) INFORMATION FOR SEQ ID NO: 7:

( i ) SEQUENCE CHARACTERISTICS:
            ( A ) LENGTH: 21
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 7:
```

GGGGAAACAC CAGAATGGAT A                                                  21

```
( 2 ) INFORMATION FOR SEQ ID NO: 8:

( i ) SEQUENCE CHARACTERISTICS:
            ( A ) LENGTH: 21
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 8:
```

ATCATATGCC CACTGTACCA T                                                  21

```
( 2 ) INFORMATION FOR SEQ ID NO: 9:

( i ) SEQUENCE CHARACTERISTICS:
            ( A ) LENGTH: 24
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 9:
```

GGATATGGCT ATTCTGAAGT GGAA                                               24

```
( 2 ) INFORMATION FOR SEQ ID NO: 10:

( i ) SEQUENCE CHARACTERISTICS:
            ( A ) LENGTH: 29
            ( B ) TYPE: nucleic acid
            ( C ) STRANDEDNESS: single
            ( D ) TOPOLOGY: linear
```

( i i ) MOLECULE TYPE: Other nucleic acid (synthetic DNA)

( x i ) SEQUENCE DESCRIPTION: SEQ ID NO: 10:

GTTTTATCAC TTTTAAATGG TCTAACTAA 29

( 2 ) INFORMATION FOR SEQ ID NO: 11:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 11:

AAGCGCCCAC AAACAGTGTA CGG 23

( 2 ) INFORMATION FOR SEQ ID NO: 12:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 12:

AAGCAGTAGA CGACAGCACC CGA 23

( 2 ) INFORMATION FOR SEQ ID NO: 13:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 13:

AGGGCGCCAT GAGACTGAAA CAC 23

( 2 ) INFORMATION FOR SEQ ID NO: 14:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 14:

CTACAAATGG CGAACATGGC GGC 23

( 2 ) INFORMATION FOR SEQ ID NO: 15:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 15:

CTAGTGGGGT GGGGGATGAT TCA 23

(2) INFORMATION FOR SEQ ID NO: 16:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 16:

AAAAATGCAA TTGTGACTGT AACAT 25

(2) INFORMATION FOR SEQ ID NO: 17:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 17:

CAATGGTAGT GCCTTCCACC TTAGG 25

(2) INFORMATION FOR SEQ ID NO: 18:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 18:

CTACTATATT GTTACCACAC AGCAA 25

(2) INFORMATION FOR SEQ ID NO: 19:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 19:

ATTGTGCAAA CGCAACAATA ATGGT 25

(2) INFORMATION FOR SEQ ID NO: 20:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 20:

ATGACAAATC TTGATACTGC ATCCA 25

( 2 ) INFORMATION FOR SEQ ID NO: 21:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 21:

AATATTGGTG GGATACATGA CAATG        25

( 2 ) INFORMATION FOR SEQ ID NO: 22:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 22:

ACAGCATATG ACACAACAAG AGTAA        25

( 2 ) INFORMATION FOR SEQ ID NO: 23:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 23:

TTTATGGATA TTATTGGTTT ACATAG        26

( 2 ) INFORMATION FOR SEQ ID NO: 24:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 24:

TCTGAAAAAA AATAGGGAAT ACGTTT        26

( 2 ) INFORMATION FOR SEQ ID NO: 25:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 25:

CCCTGTTACA AATATATCAG ATACA        25

( 2 ) INFORMATION FOR SEQ ID NO: 26:

( i ) SEQUENCE CHARACTERISTICS:
        ( A ) LENGTH: 25

(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO: 26:

TTCTGTTACA CAGTCTTATC TTACC 25

(2) INFORMATION FOR SEQ ID NO: 27:

(i) SEQUENCE CHARACTERISTICS:
(A) LENGTH: 25
(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO: 27:

CCATCTGTAC CCTCTACATC TTTAT 25

(2) INFORMATION FOR SEQ ID NO: 28:

(i) SEQUENCE CHARACTERISTICS:
(A) LENGTH: 25
(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO: 28:

CCTTTGCATT TTTTAAATAT TCGCC 25

(2) INFORMATION FOR SEQ ID NO: 29:

(i) SEQUENCE CHARACTERISTICS:
(A) LENGTH: 25
(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO: 29:

ATAATGTACA CACCCAATG CAACA 25

(2) INFORMATION FOR SEQ ID NO: 30:

(i) SEQUENCE CHARACTERISTICS:
(A) LENGTH: 26
(B) TYPE: nucleic acid
(C) STRANDEDNESS: single
(D) TOPOLOGY: linear (i i) MOLECULE TYPE: Other nucleic acid (synthetic DNA)

(x i) SEQUENCE DESCRIPTION: SEQ ID NO: 30:

AGGGCTGGTA CTGTGGGGGA AACTGT 26

(2) INFORMATION FOR SEQ ID NO: 31:

(i) SEQUENCE CHARACTERISTICS:
(A) LENGTH: 26
(B) TYPE: nucleic acid
(C) STRANDEDNESS: single
(D) TOPOLOGY: linear ( i i ) MOLECULE TYPE: Other nucleic acid (synthetic DNA)

( x i ) SEQUENCE DESCRIPTION: SEQ ID NO: 31:

GCTTTTTGTA GCCAATATGG TTTATT  26

( 2 ) INFORMATION FOR SEQ ID NO: 32:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 32:

AATTAAGGGT AGTGGAAATC GCACG  25

( 2 ) INFORMATION FOR SEQ ID NO: 33:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 33:

GGTAAAAGGG GGTAATAACA GATCA  25

( 2 ) INFORMATION FOR SEQ ID NO: 34:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 34:

GTCTACTGCA AATTTAGCCA GTTCA  25

( 2 ) INFORMATION FOR SEQ ID NO: 35:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 35:

TATGCCTGCT TCACCTGGCA GCTGT  25

( 2 ) INFORMATION FOR SEQ ID NO: 36:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 36:

ACTACTGCCT CTATTCAAAG CAGTG 25

( 2 ) INFORMATION FOR SEQ ID NO: 37:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 37:

AATTAGNGAA TATAGACATT 20

( 2 ) INFORMATION FOR SEQ ID NO: 38:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 38:

TATGGCTATT CTGAAGTGGA AGCTGNNNNN CNACAGAT 38

( 2 ) INFORMATION FOR SEQ ID NO: 39:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 39:

TTAGTTAGAC CATTTAAAAG TGATAAAACA ACNTGTNCAG ATTGG 45

( 2 ) INFORMATION FOR SEQ ID NO: 40:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 40:

TGGATANAAA GACAAACNGT TATACAACAT AGTTTNGATG AT 42

( 2 ) INFORMATION FOR SEQ ID NO: 41:

( i ) SEQUENCE CHARACTERISTICS:
        ( A ) LENGTH: 46
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 41:

TGGATAAAAT ATAGATGTNC TAAAATAGAT GATGGAGGAA ATTGGA 46

( 2 ) INFORMATION FOR SEQ ID NO: 42:

( i ) SEQUENCE CHARACTERISTICS:
  ( A ) LENGTH: 49
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 42:

CATTTTTAAG TGCATTAAAA TTATTTTGC AAGGNACNAA NAAAAAAA 49

( 2 ) INFORMATION FOR SEQ ID NO: 43:

( i ) SEQUENCE CHARACTERISTICS:
    ( A ) LENGTH: 43
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 43:

GTTGGACATA TATNGATACN TATATGAGAA ATGCGTTAGA TGG 43

( 2 ) INFORMATION FOR SEQ ID NO: 44:

( i ) SEQUENCE CHARACTERISTICS:
    ( A ) LENGTH: 40
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 44:

TCAAAGACTA AAGCACATAA AGCNATTGAA CTGCAAATGG 40

( 2 ) INFORMATION FOR SEQ ID NO: 45:

( i ) SEQUENCE CHARACTERISTICS:
    ( A ) LENGTH: 50
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 45:

CATTTAAAAG GTGANTCNAA TAGTTTAAAA TGTTTAAGAT ATAGCAGATT 50

( 2 ) INFORMATION FOR SEQ ID NO: 46:

( i ) SEQUENCE CHARACTERISTICS:
    ( A ) LENGTH: 50
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 46:

TCTATTGTGT CNTTAATNGA AGAATCTAGT NTTATTAATG CAGGTGCACC 50

( 2 ) INFORMATION FOR SEQ ID NO: 47:

( i ) SEQUENCE CHARACTERISTICS:
    ( A ) LENGTH: 50
    ( B ) TYPE: nucleic acid ( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 47:

TACATAGGCC TGCTATAACN TCCAGNCGTG GTNNTGTGCG NTTTAGTAGA    50

( 2 ) INFORMATION FOR SEQ ID NO: 48:

( i ) SEQUENCE CHARACTERISTICS:
( A ) LENGTH: 51
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 48:

CGTAAACGTN TTCCCTATTT TTTTNCAGAT GTCTNTGTGG CGGCCTAGTG A    51

( 2 ) INFORMATION FOR SEQ ID NO: 49:

( i ) SEQUENCE CHARACTERISTICS:
( A ) LENGTH: 34
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 49:

GTTGTNANCA CGGATGANTA TGTTACTCGC ACAA    34

( 2 ) INFORMATION FOR SEQ ID NO:50:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 50:

GTTGGACATC CATATTTT    18

( 2 ) INFORMATION FOR SEQ ID NO: 51:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 51:

CAATATAGGG TATTTAGGGT NCNGTTACC    29

( 2 ) INFORMATION FOR SEQ ID NO: 52:

( i ) SEQUENCE CHARACTERISTICS:
( A ) LENGTH: 36
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 52:

AATAAATTTG GATTNCCTGA CACCTCNNTT TATAAT 36

( 2 ) INFORMATION FOR SEQ ID NO: 53:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 53:

GATGGTGATA TGGTTGATAC AGGCTTTGGT GCTATGGA 38

( 2 ) INFORMATION FOR SEQ ID NO: 54:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 54:

CATTNCANGC NAATAAANGT GATGTTCCTN TNGATATTTG T 41

( 2 ) INFORMATION FOR SEQ ID NO: 55:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 55:

AAATATCCAG ATTATTTANA AATGG 25

( 2 ) INFORMATION FOR SEQ ID NO: 56:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 56:

GTTACNTCTG ANGCNCAATT ATTTAATAAA CCATATTGGC TACAANNNGC ACA 53

( 2 ) INFORMATION FOR SEQ ID NO: 57:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 57:

AATGGTATTT GTTGGGGTAA TCAATTATTT GTTACTGTGG TAGATACC 48

( 2 ) INFORMATION FOR SEQ ID NO: 58:

( i ) SEQUENCE CHARACTERISTICS:
        ( A ) LENGTH: 47
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 58:

TTTTGGGAGG TTAATTTAAA NGAAAAGTTT TCTGCAGANT TAGATCA      47

( 2 ) INFORMATION FOR SEQ ID NO: 59:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 59:

AAGTTGTAAG CACGGATGAA TATGT      25

( 2 ) INFORMATION FOR SEQ ID NO: 60:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 60:

ACATATTCAT CCGTGCTTAC AACT      24

( 2 ) INFORMATION FOR SEQ ID NO: 61:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 61:

TGCACGCACA AACATATATT ATCA      24

( 2 ) INFORMATION FOR SEQ ID NO: 62:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 62:

ATGATAATAT ATGTTTGTGC GTGCA      25

( 2 ) INFORMATION FOR SEQ ID NO: 63:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( x i ) SEQUENCE DESCRIPTION: SEQ ID NO: 63:

ACCTGTTGGT AAAAGGGGGT AATAA                     25

( 2 ) INFORMATION FOR SEQ ID NO: 64:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 64:

TTATTACCCC CTTTTACCAA CAGG                      24

( 2 ) INFORMATION FOR SEQ ID NO: 65:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 65:

CAGATCATCT GTAGCTAGTA GTAT                      24

( 2 ) INFORMATION FOR SEQ ID NO: 66:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 66:

ATACTACTAG CTACAGATGA TCTG                      24

( 2 ) INFORMATION FOR SEQ ID NO: 67:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) MOLECULE TYPE: Other nucleic acid (synthetic DNA)

( x i ) SEQUENCE DESCRIPTION: SEQ ID NO: 67:

ATTTATACAT TAAAGGCTCT GGGTC                     25

( 2 ) INFORMATION FOR SEQ ID NO: 68:

( i ) SEQUENCE CHARACTERISTICS:
    ( A ) LENGTH: 24
    ( B ) TYPE: nucleic acid
    ( C ) STRANDEDNESS: single ( D ) TOPOLOGY: linear ( i i ) MOLECULE TYPE: Other nucleic acid (synthetic DNA)

( x i ) SEQUENCE DESCRIPTION: SEQ ID NO: 68:

GACCCAGAGC CTTTAATGTA TAAA                     24

( 2 ) INFORMATION FOR SEQ ID NO: 69:

( i ) SEQUENCE CHARACTERISTICS:
      ( A ) LENGTH: 24
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 69:

TACTGCAAAT TTAGCCAGTT CAAA                     24

( 2 ) INFORMATION FOR SEQ ID NO: 70:

( i ) SEQUENCE CHARACTERISTICS:
      ( A ) LENGTH: 25
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 70:

ATTTGAACTG GCTAAATTTG CAGTA                    25

( 2 ) INFORMATION FOR SEQ ID NO: 71:

( i ) SEQUENCE CHARACTERISTICS:
      ( A ) LENGTH: 25
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 71:

CCTTATATAT TAAAGGCACA GGTAT                    25

( 2 ) INFORMATION FOR SEQ ID NO: 72:

( i ) SEQUENCE CHARACTERISTICS:
      ( A ) LENGTH: 24
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 72:

ATACCTGTGC CTTTAATATA TAAG                     24

( 2 ) INFORMATION FOR SEQ ID NO: 73:

( i ) SEQUENCE CHARACTERISTICS:
      ( A ) LENGTH: 24
      ( B ) TYPE: nucleic acid
      ( C ) STRANDEDNESS: single
      ( D ) TOPOLOGY: linear ( i i ) MOLECULE TYPE: Other nucleic acid (synthetic DNA)

( x i ) SEQUENCE DESCRIPTION: SEQ ID NO: 73:

GCCTGCTTCA CCTGGCAGCT GTGT     24

( 2 ) INFORMATION FOR SEQ ID NO: 74:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 74:

CACACAGCTG CCAGGTGAAG CAGGC     25

( 2 ) INFORMATION FOR SEQ ID NO: 75:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 75:

AGGGGGTAAT AACAGATCAT CTGT     24

( 2 ) INFORMATION FOR SEQ ID NO: 76:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 76:

ACAGATGATC TGTTATTACC CCCT     24

( 2 ) INFORMATION FOR SEQ ID NO: 77:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 77:

AGGCTCTGGG TCTACTGCAA ATTT     24

( 2 ) INFORMATION FOR SEQ ID NO: 78:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 78:

AAATTTGCAG TAGACCCAGA GCCT     24

( 2 ) INFORMATION FOR SEQ ID NO: 79:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 79:

AGGCACAGGT ATGCCTGCTT CACC                    24

( 2 ) INFORMATION FOR SEQ ID NO: 80:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 80:

GGTGAAGCAG GCATACCTGT GCCT                    24

( 2 ) INFORMATION FOR SEQ ID NO: 81:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 81:

GCTGCAAACA ACTATACATG ATATAA                  26

( 2 ) INFORMATION FOR SEQ ID NO: 82:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 82:

TTATATCATG TATAGTTGTT TGCAGC                  26

( 2 ) INFORMATION FOR SEQ ID NO: 83:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 83:

TATTAGAATG TGTGTACTGC AAGCA                   25

( 2 ) INFORMATION FOR SEQ ID NO: 84:

( i ) SEQUENCE CHARACTERISTICS:

(A) LENGTH: 25
    (B) TYPE: nucleic acid
    (C) STRANDEDNESS: single
    (D) TOPOLOGY: linear ( i i ) MOLECULE TYPE: Other nucleic acid (synthetic DNA)

( x i ) SEQUENCE DESCRIPTION: SEQ ID NO: 84:

TGCTTGCAGT ACACACATTC TAATA 25

( 2 ) INFORMATION FOR SEQ ID NO: 85:

( i ) SEQUENCE CHARACTERISTICS:
        (A) LENGTH: 24
        (B) TYPE: nucleic acid
        (C) STRANDEDNESS: single
        (D) TOPOLOGY: linear ( i i ) MOLECULE TYPE: Other nucleic acid (synthetic DNA)

( x i ) SEQUENCE DESCRIPTION: SEQ ID NO: 85:

CTTCACTGCA AGACATACAA ATAA 24

( 2 ) INFORMATION FOR SEQ ID NO: 86:

( i ) SEQUENCE CHARACTERISTICS:
        (A) LENGTH: 23
        (B) TYPE: nucleic acid
        (C) STRANDEDNESS: single
        (D) TOPOLOGY: linear ( i i ) MOLECULE TYPE: Other nucleic acid (synthetic DNA)

( x i ) SEQUENCE DESCRIPTION: SEQ ID NO: 86:

TTATTTCTAT GTCTTGCAGT GAA 23

( 2 ) INFORMATION FOR SEQ ID NO: 87:

( i ) SEQUENCE CHARACTERISTICS:
        (A) LENGTH: 24
        (B) TYPE: nucleic acid
        (C) STRANDEDNESS: single
        (D) TOPOLOGY: linear ( i i ) MOLECULE TYPE: Other nucleic acid (synthetic DNA)

( x i ) SEQUENCE DESCRIPTION: SEQ ID NO: 87:

CCTGTGTATA TTGCAAGACA GTAT 24

( 2 ) INFORMATION FOR SEQ ID NO: 88:

( i ) SEQUENCE CHARACTERISTICS:
        (A) LENGTH: 23
        (B) TYPE: nucleic acid
        (C) STRANDEDNESS: single
        (D) TOPOLOGY: linear ( i i ) MOLECULE TYPE: Other nucleic acid (synthetic DNA)

( x i ) SEQUENCE DESCRIPTION: SEQ ID NO: 88:

TACTGTCTTG CAATATACAC AGG 23

( 2 ) INFORMATION FOR SEQ ID NO: 89:

( i ) SEQUENCE CHARACTERISTICS:
        (A) LENGTH: 24
        (B) TYPE: nucleic acid
        (C) STRANDEDNESS: single
        (D) TOPOLOGY: linear ( i i ) MOLECULE TYPE: Other nucleic acid (synthetic DNA)

( x i ) SEQUENCE DESCRIPTION: SEQ ID NO: 89:

TATATTGCAA GACAGTATTG GAAC      24

( 2 ) INFORMATION FOR SEQ ID NO: 90:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 90:

GTTCCAATAC TGTCTTGCAA TTTA      24

( 2 ) INFORMATION FOR SEQ ID NO: 91:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 91:

TTACAGAGGT ATTTGAATTT GCATT      25

( 2 ) INFORMATION FOR SEQ ID NO: 92:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 92:

AATGCAAATT CAAATACCTC TGTAA      25

( 2 ) INFORMATION FOR SEQ ID NO: 93:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 93:

GTATGGAACA ACATTAGAAC AGCA      24

( 2 ) INFORMATION FOR SEQ ID NO: 94:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 94:

TGCTGTTCTA ATGTTGTTCC ATAC    24

( 2 ) INFORMATION FOR SEQ ID NO: 95:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 95:

ATACAACAAA CCGTTGTGTG ATTT    24

( 2 ) INFORMATION FOR SEQ ID NO: 96:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO: 96:

AAATCACACA ACGGTTTGTT GTAT    24

NUCLEOTIDE SEQUENCES USEFUL AS TYPE SPECIFIC PROBES, PCR PRIMERS AND LCR PROBES FOR THE AMPLIFICATION AND DETECTION OF HUMAN PAPILLOMA VIRUS, AND RELATED KITS AND METHODS

This application is a continuation of U.S. patent application Ser. No. 07/965,665, filed Oct. 22, 1992, now abandoned, which is a continuation-in-part (CIP) of U.S. patent applications Ser. Nos 07/589,948, 07/590,105, and 07/590,253, all filed on Sep. 28, 1990 and now abandoned. The entire disclosure of each of these applications is incorporated herein by reference.

BACKGROUND OF THE INVENTION

This invention relates generally to human papilloma virus, and more particularly, relates to nucleotide sequences of short strands of human papilloma virus which can be amplified and/or used to determine the presence of human papilloma virus products in a test sample, and which also can be amplified and/or used to determine the specific type of human papilloma virus of types 6, 11, 16, 18, 31, 33 and 61 present in the test sample.

Human papilloma virus (HPV) is recognized as a venereally-transmitted disease of the anogenital tract which often is associated with the pathogenesis of cervical cancer and its precursor lesions. More than 56 types of HPV have been characterized. Of these, at least 21 types infect the anogenital tract. L. Gregoire et al., *J. Clin. Micro* 27 (12):2660–2665(1989). These mucosotropic viruses are associated most frequently with benign condyloma or latent infections. However, the presence of HPV in premalignant lesions and invasive cancers, particularly of the cervix, may reflect the oncogenic potential of these viruses. See P. M. Howley, in *Important Advances in Oncology,* D. T. DeVita, Jr. et al., eds., J. B. Lippincott, Philadelphia, Pa. (1987) at pages 55–73.

Certain HPV types, namely, HPV type 16 and type 18, and to a lesser extent HPV types 31, 33 and 35, are found in a high proportion of invasive cervical cancers and their metastases. However, many HPV types which infect the anogenital tract, such as HPV types 6 and 11, are found most commonly in benign condyloma and only rarely are found in invasive cancers. HPV detected in the anogenital tract can be classified broadly as low risk papilloma viruses (HPV types 6 and 11), intermediate risk papilloma viruses (HPV types 31, 33 and 35) or high risk papilloma viruses (HPV types 16 and 18), based on the association of the particular HPV type with malignancy. A. T. Lorincz et al., *J. Nat'l. Cancer Inst.* 79:671 (1987). Thus, the detection of the presence of HPV and the determination of the specific type of HPV can provide a diagnostic and prognostic tool useful for determining the clinical significance associated with certain HPV types. The early detection of HPV by sensitive and specific reagents and methodologies also could provide earlier therapeutic management and counseling.

A need therefore exists for accurate and reliable methods to identify and type HPV in clinical specimens. However, known polyclonal antisera prepared by immunizing animals with disrupted virions are capable of detecting HPV antigens in only about 30–70% of cutaneous and mucosal warts. Further, the antisera are broadly cross-reactive. Available immunological tests have two major drawbacks. First, only well-differentiated cells apparantly are capable of viral antigen expression. HPV-infected tissues which show higher degrees of neoplasia, such as carcinoma in situ, rarely contain HPV antigen. Thus, the further the development of the malignancy, the smaller the amount of detectable virus in the tested tissue. Secondly, these immunological tests are unable to identify specific viral types.

It is known that papilloma viruses share amino acid sequences in the major capsid proteins. See, for example, C. C. Baker, in *The Papovaviridae* (Vol. 2), P. M. Howley and N. P. Salzman, eds., Plenum Publ. Corp., New York (1987) at pages 321–385. The DNAs of this virus cross-hybridize, indicating homologous sequences. M. F. Law et al., *J. Virol.* 58:225–229 (1979). Thus, molecular hybridization techniques have been developed as a more sensitive and specific means of detecting and differentiating HPV DNA and RNA in clinical specimens. See A. T, Lorinez, *Obstetrics and Gynecol, Clinics of N. America* 14:451 (1987).

Sequences specific for the DNA and RNA of human papilloma virus are known and have been published. See, for example, PCT application No. WO 89/69940 published Oct. 19, 1989, PCT application No. WO 86/05816 published Oct. 9, 1986 and European Patent Application No. 0 301 968 published Feb. 1, 1989.

The molecular hybridization techniques used to detect homologous DNA sequences are sensitive and can be highly specific if used with probes which bind to nucleic acid sequences which are unique to a particular HPV type. However, the concentration of total viral DNA in a given clinical sample may be below the limit of sensitivity of the test. For example, the amount of viral DNA in dysplastic cervical lesions is reduced with increasing dysplasia.

To overcome this problem of sensitivity, viral DNA sequences can be amplified by using, for example, the polymerase chain reaction (PCR) or the ligase chain reaction (LCR) techniques. The products thus obtained can be identified by using conventional hybridization techniques for identification of virus types, such as Southern blotting. See C. Oste, *Biotechniques* 6:163 (1988), K. B. Mullis, U.S. Pat. No. 4,683,202, and EP-A-320 308 (BioTechnica).

Both PCR and LCR serve to amplify the DNA present in a test sample to detectable levels. In practice, the level of sensitivity is about 50 to 100 copies per sample. The next most sensitive technique is dot-blot, which can detect about 10,000 molecules, while Southern blot reliably detects about 100,000 copies of DNA per sample.

Thus, the appropriate diagnosis of HPV may require two steps. In one strategy, the presence of a clinically relevant type of HPV is first detected with a group-specific primer. After the presence of HPV is detected, differentiation between types can be performed by using a type-specific probe having low homology between the HPVs of the group. Alternatively, differentiation can be performed using a mixture of type-specific probes at the outset, provided these probes amplify DNA independently of each other, and that they can be detected independently. In the past, such tasks were attempted using specific antibodies. In general, nucleic acid probes and primers allow greater discrimination among subtypes than do antibodies. The use of DNA-based tests increases both sensitivity and specificity over prior-art antibody-based tests.

It therefore would be advantageous to provide oligonucleotide strands of DNA which could be amplified and used to detect the presence, if any, of HPV in a test sample. It also would be advantageous to provide short oligonucleotide strands of DNA which could be amplified and used to detect the presence, if any, of specific types of HPV in the test sample. The combined use of oligonucleotide strands would be advantgeous for allowing for the specific and sensitive in vitro diagnosis of the presence and specific type of HPV present in test samples.

SUMMARY OF THE INVENTION

Oligonucleotides of from about 10 to about 60 nucleotides are provided which can be amplified and used either to detect specific sequences of specific types of human papilloma virus, or consensus regions with high homology among different types. The presence of HPV is determined by contacting the test sample with sequences provided to detect the presence, if any, of HPV types 6, 11, 16, 18, 31, 33 and 61. This may be done with or without prior amplification, for example, by PCR or LCR. Either type-specific or consensus amplification is also possible. Two oligonucleotides are provided if the sequence is to be amplified by PCR, and four oligonucleotides provided if amplification is by LCR, in accordance with these known amplification procedures. After the presence of HPV is detected, the type of HPV present in the sample can be determined by using HPV type-specific probes, by subsequent rounds of PCR, or by LCR. Alternatively, the presence of type-specific HPV can be determined by contacting the test sample directly with type-specific nucleotide sequence provided by the invention for the detection of HPV types 6, 11, 16, 18, 31, 33 and 61. Also provided are methods for using the oligonucleotides and kits for amplifying and detecting the presence of human papilloma virus.

DETAILED DESCRIPTION OF THE INVENTION

Figure 1:
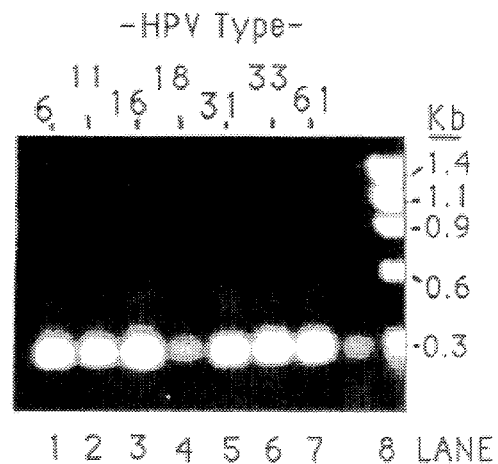
FIG. 1 is a photograph of a gel following electrophoresis showing the results when the primers PCR1 and PCR5 were used to amplify selected plasmids wherein HPV 6 is in lane 1, HPV 11 is in lane 2, HPV 16 is in lane 3, HPV 18 is in lane 4, and HPV 31 is lane 5, HPV 33 is in lane 6, HPV 61 is in lane 7, and molecular weight standards are in lane 8.

The appropriate diagnosis of HPV requires two sets of conditions. The first enables the detection of all pertinent types, and the second set allows differentiation among them. In the past, such tasks have been attempted using specific antibodies. In general, nucleic acid probes and primers allow greater discrimination among subtypes than do antibodies. Thus, the use of DNA-based tests tends to increase both sensitivity and specificity over antibody-based tests.

U.S. Pat. Nos. 4,683,195 and 4,683,202 teach a method of amplifying DNA sequences by using PCR. This method now is a standard procedure in many molecualr biology laboratories. Examples 1–4 which follow below utilize the procedures taught in these two patents and the method as described in the package insert of the commercially-available Gene-Amp™ kit (Document No. 55635-6/89, Perkin-Elmer/Cetus, Emeryville, Calif.).

In PCR, two complementary polynucleotide strands are amplified by treating the strands with two oligonucleotide primers such that an extension product of each primer is synthesized Which is complementary to each nucleic acid strand. The primers are selected such that the extension product of one primer forms a template for the synthesis of an extension product from the other primer once the extension product of the one primer is separated from the template. A chain reaction is maintained by a cycle of denaturing the primer extension products from their templates, treating the single-stranded molecule generated with the same primers to re-anneal, and allowing the primers to form further extension products. The cycle is repeated for any many times as it takes to increase the target nucleic acid segments to a concentration where they can be detected.

The amplified target sequence can be detected by any of several known techniques; for example, by denaturing the double-stranded products formed by PCR, and treating those products with one or more reporter probes which hybridize with the extension products. The reporter probe has a detectable label, and usually is added in excess. The unhybridized reporter probe, therefore, must be separated from the hybridized reporter probe by involving a separation step. In another method of detecting the extension products without reporter probe and a separation step, the extension products are detected by gels stained with ethidium bromide. The diagnosis can be confirmed by transferring the DNA to nitrocellulose and probing with a probe specific to the HPV type suspected of being present in the sample.

Alternately with PCR, one may take advantage of known restriction sites within the HPV DNA to demonstrate that the amplified DNA contains the expected sequence by examining the cleavage pattern(s) generated with one or more restriction endonucleases. Verifying the authenticity of the amplified sequence may be necessary for two reasons: (1) to ensure that sequences complementary to the amplifying primers are not fortuitously present in cellular DNA which does not contain HPV DNA, and (2), to identify the type of HPV present in the sample. If the sequences chosen for amplification are conserved among HPV types, then the finding of an amplified product does not implicate a particular HPV type. It also should be possible to predict the size of the amplified product based on the binding positions of the two primers. Thus, when that product is found, one reasonably can be assured that HPV is present. However, two different types of HPV may give the same or different size products. Thus, hybridization should be used to confirm the identity of the amplified sequence until confidence is built that the interpretation of the results is reliable. It should be pointed out that the PCR technique will identify only closely related, or type-specific sequences in the absence of highly homologous primers, since only a small portion of the genome is analyzed.

Another particularly useful detection technique is described in EP-A-357 011. In this method, a different reporter molecule, e.g. hapten, is attached to each primer. Following amplification, but before denaturation, duplexes can be detected by "capturing" one hapten (hapten1) with a solid phase coated with anti-hapten1. The separated complex can be detected with a conjugate of label and anti-hapten2, and label associated with the solid phase can be measured.

The Ligase Chain Reaction (LCR) amplifies sections of DNA by copying the section of DNA, and copying the copies of that section of DNA, many times over. This method is 35 described in European Patent Application No. 0 320 308 published Jun. 14, 1989, and in European Patent Application No. 0 439 182 published Jul. 31, 1991, both of which are incorporated herein by reference. In this procedure, two probes (for example, A and B) complementary to immediately adjacent regions of a target sequence are hybridized and ligated. This ligated probe then is denatured away from the target, after which it is hybridized with two additional probes (A' and B') of sense opposite to the initial probes A and B. The secondary probes are themselves then ligated. Subsequent cycles of denaturation/hybridization/ligation create the formation of double-length probes of both sense (+) and antisense (−).

In LCR, the nucleic acid of the sample is provided either as single stranded DNA or as double-stranded DNA which is denatured to separate the strands. Four probes are utilized: the first two probes (A and B) are the so-called primary probes, and the second two probes (A' and B') are the so-called secondary probes. The first probe (A) is a single strand capable of hybridizing to a first segment of the primary strand of the target nucleotide sequence. The second probe (b) is capable of hybridizing to a second segment of the primary strand of the target nucleotide sequence. The 5' end of the first segment of the primary strand of the target is positioned relative to the 3' end of the second segment of the primary strand of the target to enable joining of the 3' end of the first probe to the 5' end of the second probe, when the probes are hybridized to the primary strand of the target nucleotide sequence. The third probe (A') is capable of hybridizing to the first probe, and the fourth probe (B') is capable of hybridizing to the second probe (B). The hybridized probes are ligated to form reorganized fused probe sequences. Then, the DNA in the sample is denatured to separate ligated probes from sample DNA. Successive cycles wherein the ligated probes and target DNA undergo the above-described process are performed to increase the amount of detectable DNA in the sample. The amount of cycles performed is dependent upon the sequence used and the sensitivity required of the test. Usually, the cycle can be repeated from 15 to 60 times. At least one of the probes can be conjugated to a signal generating compound.

If the four probes are conjugated to appropriate binding members, the detection of amplified product can be accomplished using standard manual or automated immunoassay procedures known to those skilled in the art. These procedures include, for example, immunochromatography, ELISA, EIA and MEIA. Hybridization also can be accomplished by following standard dot-, slot- or replica-blot procedures which are known to those in the art. The sequences can be labelled with an appropriate signal generating compound (label), which is capable of generating a measureable signal detectable by external means. The various signal generating compounds contemplated include chromogens, catalysts such as enzymes, luminescent compounds such as fluoroscein and rhodamine, chemiluminescent compounds, radioactive elements such as $^{32}$P, and other labels known to those of ordinary skill in the art. The selection of a particular label is not critical, but it will be capable of producing a a signal either by itself or in conjunction with one or more additional substances. A variety of different indicator reagents can be formed of label and specific binding member. Either the label or a specific binding member can be varied. Examples of specific binding members which can be used as a member of the indicator reagent include antibodies, both monoclonal, polyclonal, and fragments thereof; avidin or biotin, biotin and anti-biotin, a carbohydrate or a lectin, a complementary nucleotide sequence, an effector or a receptor molecule, an enzyme cofactor or an enzyme; an enzyme inhibitor or an enzyme; also any antigenic substances, haptens, antibodies, and combinations thereof.

The test sample can be any biological material suspected of containing HPV. Thus, the test sample can be human body tissue, or a test sample which contains cells suspected of containing HPV.

The invention will now be described by way of Examples, which are meant to describe, but not to limit, the spirit and scope of the invention.

The following terms used in the examples are trademarks, tradenames or chemical abbreviations as specified:

TRIS - chemical abbreviation for [tris(hydroyxmethyl)aminomethane], used as a buffer.

EDTA - chemical abbreviation for ethylenediaminetetraacetic acid, a chelating agent.

FITC - chemical abbreviation for fluorescein isothiocyanate, a flourescent hapten derivative.

NHS-ester - chemical abbreviation for N-hydroxysuccinamide ester

MES - chemical abbreviation for [2-(N-morpholino)ethanesulfonic acid], a buffer.

TWEEN®-20 - trademark of Atlas Chemical for polyoxyethylene sorbitan monolaurate, a detergent.

BIS-TRIS - chemical abbbreviation for [bis-(2-hydroxyethyl)-amino]tris(hydroxymethyl)methane, a buffer.

TRITON X-100® - trademark of Rohm & Haas for nonaethylene glycol octylphenol ether, a detergent.

IMx® - trademark of Abbott Laboratories for an automated instrument for performing microparticle enzyme immunoassay (MEIA).

EXAMPLES

EXAMPLE 1

PCR was performed essentially following the package insert of the commercially available Gene-Amp™ kit (document No. 55635-6/89, available from Perkin-Elmer/Cetus, Emeryville, Calif.). The following reagents were mixed in a 0.5 mL polypropylene tube and used in performing PCR:

| Reagent | Final Concentration |
| --- | --- |
| Water | (to give final volume = 50 or 100 μL) |
| Reaction Buffer | 10 mM TRIS pH 8.3 |

| Reagent | Final Concentration |
|---|---|
|  | 50 mM KCl |
|  | 1.5 mM MgCl2 |
|  | 0.01% gelatin |
| dNTP mixture | 200 μM each of dATP, dCTP, dGTP, and TTP |
| PCR1 | 1 μM |
| PCR2 | 1 μM |
| plasmid | 10 μL     1 ng/100 μL |
| (or control- human placental DNA (Pooled Placental DNA, catalog D-3287, Sigma Chemical Co, St. Louis MO). | |
| DNA polymerase, Thermus Acguaticus | 25 or 63.9 units/1 mL |

After mixing, the reaction mixture was overlayed with 100 μL of mineral oil. The tube then was placed in an instrument capable of incubation at several temperatures, and subjected to 30 or 40 cycles of programmed temperature change. The precise cycle of temperature change used, and the instrument used, varied with the experiment, and is detailed in the descriptions of the figures in Example 3.

EXAMPLE 2

Following the procedure of Example 1, the following sequences were found to amplify sections of papilloma virus types 6, 11, 16, 18, 31, 33, and 61 using PCR.

| PCR1: | CAGATGTCTC | TGTGGCGGCC | TAGTG | (SEQ ID No. 1) |
|---|---|---|---|---|
| PCR5: | AGGTGTCAGG | AAAACCAAAT | TTATT | (SEQ ID No. 5) |
| PCR14: | GAATTAGTTA | GACCATTTAA | AAG | (SEQ ID No. 6) |
| PCR15: | GGGGAAACAC | CAGAATGGAT | A | (SEQ ID No. 7) |
| IWDO: | ATCATATGCC | CACTGTACCA | T | (SEQ ID No. 8) |

Sequence IWDO is derived from a sequence disclosed in International application number PCT/US86/00629 (WO 86/05816).

The following sequences were found to amplify sections of papilloma virus types 6, 11, 16, 18, and 31 using PCR. TABLE 1 shows the sequences and where they map to in the various types.

| PCR2: | CGTTTTCCAT | ATTTTTTTGC | AGATG | (SEQ ID No. 2) |
|---|---|---|---|---|
| PCR3: | AAGTTGTAAG | CACCGATGAA | TATGT | (SEQ ID No. 3) |
| PCR4: | AATGTACCCT | AAATACCCTA | TATTG | (SEQ ID No. 4) |

TABLE 1

SEQUENCES WHICH CAN BE USED AS PROBES OR PCR PRIMERS

| PROBE | SEQ ID No. | SEQUENCE | SENSE | MAPS TO: (type 6) | MAPS TO: (type 11) | MAPS TO: (type 16) | MAPS TO: (type 18) | MAPS TO: (type 31) | MAPS TO: (type 33) |
|---|---|---|---|---|---|---|---|---|---|
| PCR1: | 1 | CAGATGTCTCTGTGGCGGCCTAGTG | + | 5786–5810 | 5768–5792 | 5634–5658 | 5610–5634 | 5550–5574 | 5591–5615 |
| PCR2: | 2 | CGTTTTCCATATTTTTTTGCAGATG | + | 5767–5791 | 5749–5773 | 615–639 | 5591–5615 | 5531–5555 | 5572–5596 |
| PCR3: | 3 | AAGTTGTAAGCACCGATGAATATGT | + | 5844–5868 | 5826–5850 | 695–719 | 5671–5695 | 5611–5635 | 5652–5676 |
| PCR4: | 4 | AATGTACCCTAAATACCCTATATTG | – | 6008–5984 | 5990–5966 | 865–841 | 5841–5817 | 5784–5760 | 5825–5801 |
| PCR5: | 5 | AGGTGTCAGGAAAACCAAATTTATT | – | 6044–6020 | 6026–6002 | 5901–5877 | 5877–5853 | 5820–5796 | 5861–5837 |
| PCR14: | 6 | GAATTAGTTAGACCATTTAAAAG | + | 1495–1517 | 1495–1517 | 1524–1546 | 1595–1617 | 1462–1484 | 1518–1540 |
| PCR15: | 7 | GGGGAAACACCAGAATGGATA | + | 1834–1854 | 1834–1854 | 1863–1883 | 1934–1954 | 1801–1821 | 1857–1877 |
| IWDO: | 8 | ATCATATGCCCACTGTACCAT | – | 1931–1911 | 1931–1911 | 1960–1940 | 2031–2011 | 1898–1878 | 1954–1934 |

EXAMPLE 3

Linearized plasmids containing full-length papilloma virus inserts in pGEM3 were used as targets. These were pHPV6.1 (HPV6), pSP65.11.5 (HPV11), p65.16.8 (HPV16), pHPV18H (HPV18), pG3.HPV31 (HPV31), pLNK322.HPV33 (HPV33), and pBR322.HPV61 (HPV61). The Programmable Cyclic Reactor™ (available from Ericomp, San Diego) was used as the incubation instrument. Following PCR procedures as described in Example 1, 10 μL aliquots were analyzed by electrophoresis through agarose (comprising a 5:3 ratio of NuSieve®:SeaKem® GTG, available from the FMC Corp., Rockland, Me.) in a buffer comprising 0.089 M TRIS, 0.089 M borate, 2 mM EDTA, and 0.5 ppt ethidium bromide.

FIG. 1 is a photograph of an ethidium bromide-stained 1.2% agarose gel showing results using 63.9 units/mL DNA polymerase, in the DNA Thermal Cycler™ (Perkin-Elmer/CETUS, Emeryville, Calif.). The samples were heated for 5 minutes at 94° C., then subjected to 40 cycles of a temperature program of: 1 minute at 94° C., 2 minutes at 40° C., and 1.5 minutes at 72° C. The PCR primers used in this case were PCR1 and PCR5 of Example 2. Examination of the gel following electrophoresis showed bands at the expected positions, i.e. 292 bp. Lane 1, HPV6; lane 2, HPV11;lane 3, HPV16; lane 4, HPV18; lane 5, HPV31; lane 6, HPV33, lane 7, HPV61; lane 8, pooled human placental DNA (suspected of having HPV infection); lane 9, molecular weight markers—Hae III digest of ΦX174.

Figure 2:
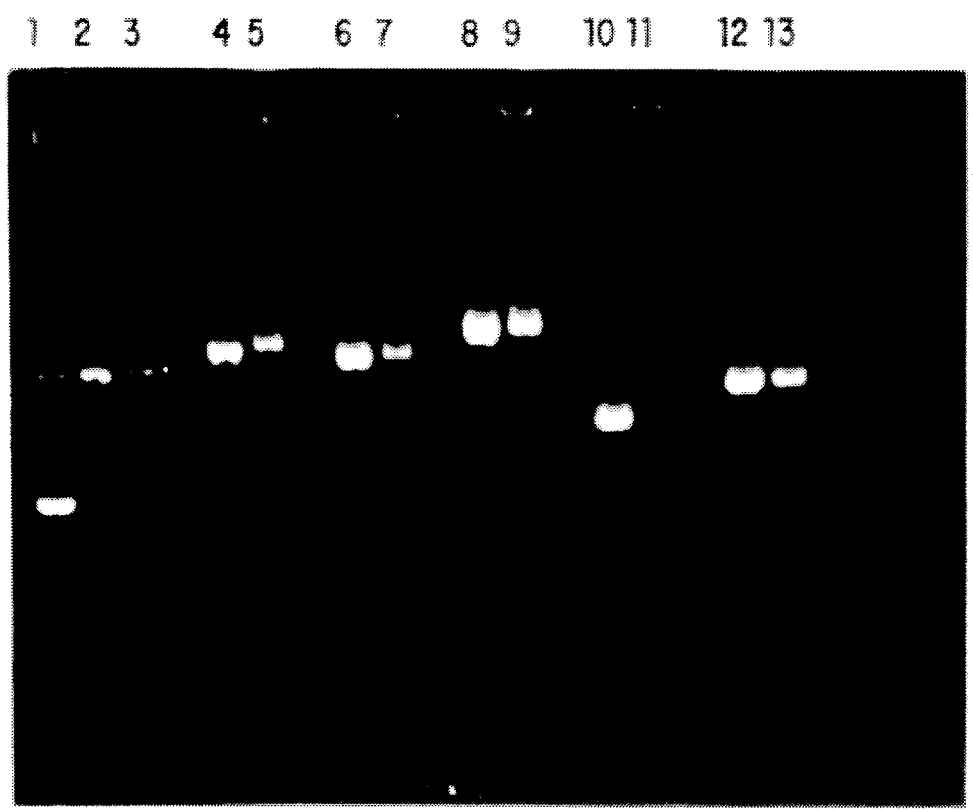
FIG. 2 is a photograph of a gel following electrophoresis showing the results when the primers PCR1, PCR2, PCR3, PCR4 and PCR5 were used to amplify plasmid p65.16.8 (HPV 16).

FIG. 2 is a photograph of an ethidium bromide-stained 4% agarose gel showing results using 25 units/mL DNA polymerase, in the Programmable Cycler Reactor™ (Ericomp, San Diego, Calif.). Samples in this case were subjected to 30 cycles of a temperature program of: 50° C. for one (1) minute, 72° C. for two (2) minutes and 95° C. for one (1) minute. In this case, the primers PCR1, PCR2, PCR3, PCR4 and PCR5 of Example 2 were used to amplify plasmid p65.16.8(HPV16). Examination of the gel of FIG. 2 shows bands at the expected positions, i.e., PCR1 and PCR4, 235 bp, lane 2; PCR1 and PCR5, 267 bp, lane 4; PCR2 and PCR4, 254 bp, lane 6; PCR2 and PCR5, 286 bp, lane 8; PCR3 and PCR4, 174 bp, lane 10; PCR3 and PCR5, 206 bp, lane 12; molecular weight marker, 123, 246, 369, 492, . . . bp ladder, lane 1.

Figure 3:
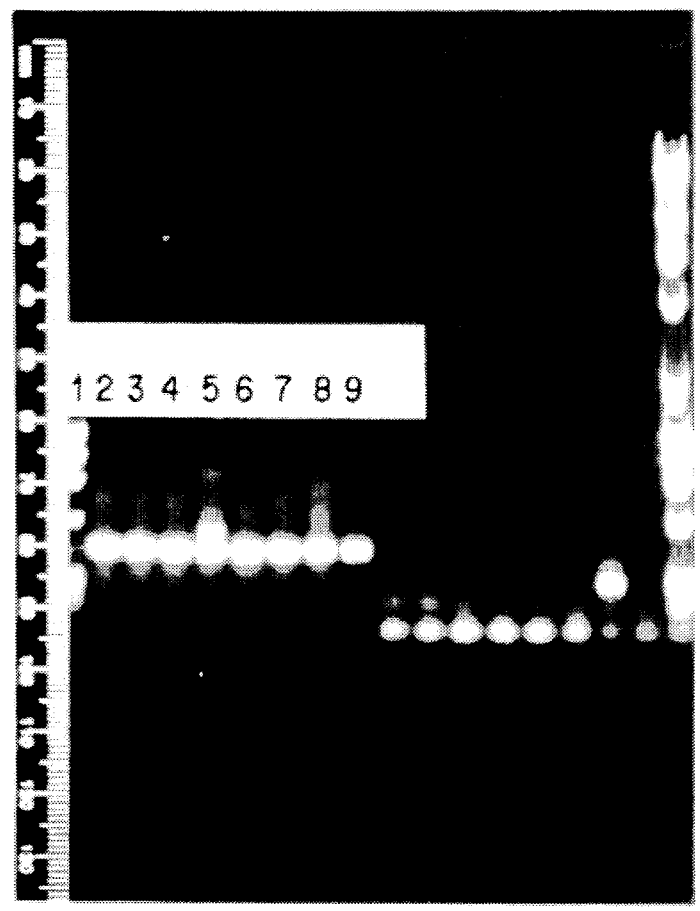
FIG. 3 is a photograph of the ethidium bromide-stained gels wherein PCR14 and PCR15 are used in conjunction with IWDO to obtain amplified PCR product.

FIG. 3 is a photograph of an ethidium bromide-stained 1.2% agarose gel showing results using the same conditions as FIG. 1. In this case, PCR14 and PCR15 were used as primers in conjunction with IWDO. The expected size of the amplified PCR product of PCR14 and IWDO is 437 bp for all of the HPV types tested. The expected size of the product of PCR15 and IWDO is 98 bp. Products of these sizes appear in the gels, confirming that PCR14 and PCR15, used in conjunction with IWDO, will amplify HPV DNA of types 6, 11, 16, 18, 31, 33, and 61. Lane 1, Molecular weight marker (Hae III digest of FX174); PCR14+IWDO, lanes 2–9: lane 2, HPV6; lane 3, HPV11; lane 4, HPV16; lane 5, HPV18; lane 6, HPV31; lane 7, HPV33; lane 8, HPV61; lane 9, human placental DNA suspected of being infected with HPV; PCR15+IWDO, lanes 10–17: lane 10, HPV6; lane 11, HPV11; lane12, HPV16; lane 13, HPV18; lane 14, HPV31; lane 15, HPV33; lane 16, HPV61; lane 17, human placental DNA suspected of being infected with HPV; lane 18, molecular weight marker (Hae III digest of FX174 and Hind III digest of I DNA).

EXAMPLE 4

Four regions were selected because they allowed two processes to occur simultaneously: nonspecific amplification and specific detection. At their boundaries, these regions contained areas of high homology such that any of HPV types 6, 11, 16, 18 or 33 could be amplified by PCR using one set of primers. In their interiors, these regions contained areas of low homology, such that probes specific for any one of these papilloma types may hybridize with its specific complementary counterpart and not any other.

The following sets of sequences were designed to be used in combination in order to take advantge of the four regions described above in this Example. Two members of each set, designated at PCRn, recognize any of papilloma virus types 6, 11, 16, 18 and 33. The other members designated as PROBEn, recognize only one specific type used in conjunction with each other in the particular set. Tables 2–5 show the sequences and where they map to in the various types.

|  | SEQUENCE | | | SEQ ID No. |
|---|---|---|---|---|
| SET 1: | | | | |
| PCR6: | GGATATGGCT | ATTCTGAAGT | GGAA | 9 |
| PCR7: | GTTTTATCAC | TTTTAAATGG | TCTAACTAA | 10 |
| PROBE6a: | AAGCGCCCAC | AAACAGTGTA | CGG | 11 |
| PROBE11a: | AAGCAGTAGA | CGACAGCACC | CGA | 12 |
| PROBE16a: | AGGGCGCCAT | GAGACTGAAA | CAC | 13 |
| PROBE18a: | CTACAAATGG | CGAACATGGC | GGC | 14 |
| PROBE33a: | CTAGTGGGGT | GGGGGATGAT | TCA | 15 |
| SET 2: | | | | |
| PCR8: | AAAAATGCAA | TTGTGACTGT | AACAT | 16 |
| PCR9: | CAATGGTAGT | GCCTTCCACC | TTAGG | 17 |
| PROBE6b: | CTACTATATT | GTTACCACAC | AGCAA | 18 |
| PROBE11b: | ATTGTGCAAA | CGCAACAATA | ATGGT | 19 |
| PROBE 16b: | ATGACAAATC | TTGATACTGC | ATCCA | 20 |
| PROBE 18b: | AATATTGGTG | GGATACATGA | CAATG | 21 |
| PROBE33b: | ACAGCATATG | ACACAACAAG | AGTAA | 22 |
| SET 3: | | | | |
| PCR10: | TTTATGGATA | TTATTGGTTT | ACATAG | 23 |
| PCR11: | TCTGAAAAAA | AATAGGGAAT | ACGTTT | 24 |
| PROBE6c: | CCCTGTTACA | AATATATCAG | ATACA | 25 |
| PROBE11c: | TTCTGTTACA | CAGTCTTATC | TTACC | 26 |

-continued

| | SEQUENCE | | | SEQ ID No. |
|---|---|---|---|---|
| PROBE16c: | CCATCTGTAC | CCTCTACATC | TTTAT | 27 |
| PROBE18c: | CCTTTGCATT | TTTTAAATAT | TCGCC | 28 |
| PROBE33c: | ATAATGTACA | CACCCCAATG | CAACA | 29 |
| SET 4: | | | | |
| PCR12: | AGGGCTGGTA | CTGTGGGGGA | AACTGT | 30 |
| PCR13: | GCTTTTTGTA | GCCAATATGG | TTTATT | 31 |
| PROBE6d: | AATTAAGGGT | AGTGGAAATC | GCACG | 32 |
| PROBE11d: | GGTAAAAGGG | GGTAATAACA | GATCA | 33 |
| PROBE16d: | GTCTACTGCA | AATTTAGCCA | GTTCA | 34 |
| PROBE18d: | TATGCCTGCT | TCACCTGGCA | GCTGT | 35 |
| PROBE33d: | ACTACTGCCT | CTATTCAAAG | CAGTG | 36 |

TABLE 2

SEQUENCES WHICH CAN BE USED: 1) TOGETHER AS GENERAL PROBES OR PCR PRIMERS, AND 2) AS TYPE-SPECIFIC PROBES
SET "a"

| PROBE | SEQ ID No. | SEQUENCE | MAP POSITION: | | | | |
|---|---|---|---|---|---|---|---|
| | | | TYPE 6 | TYPE 11 | TYPE 16 | TYPE 18 | TYPE 33 |
| A-PCR6: | 9 | GGATATGGCAATTCTGAAGTGGAA | 1237–1260 | 1237–1260 | 1260–1283 | 1319–1342 | 1272–1295 |
| B-PCR7: | 10 | GTTTTATCACTTTTAAATGGTCTAACTAA | 1526–1498 | 1526–1498 | 1355–1327 | 1626–1598 | 1549–1521 |
| PROBE6: | 11 | AAGCGCCCACAAACAGTGTACGG | 1370–1392 | | | | |
| PROBE11: | 12 | AAGCAGTAGACGACAGCACCCGA | | 1370–1392 | | | |
| PROBE16: | 13 | AGGGCGCCATGAGACTGAAACAC | | | 1307–1329 | | |
| PROBE18: | 14 | CTACAAATGGCGAACATGGCGGC | | | | 1362–1384 | |
| PROBE33: | 15 | CTAGTGGGGTGGGGGATGATTCA | | | | | 1360–1382 |

TABLE 3

SEQUENCES WHICH CAN BE USED: 1) TOGETHER AS GENERAL PROBES OR PCR PRIMERS, AND 2) AS TYPE-SPECIFIC PROBES
SET "b"

| PROBE | SEQ ID No. | SEQUENCE | MAP POSITION: | | | | |
|---|---|---|---|---|---|---|---|
| | | | TYPE 6 | TYPE 11 | TYPE 16 | TYPE 18 | TYPE 33 |
| A-PCR8: | 16 | AAAAATGCAATTGTGACTGTAACAT | 3707–3731 | 3704–3728 | 3739–3763 | 3801–3825 | 3697–3721 |
| B-PCR9: | 17 | CAATGGTAGTGCCTTCCACCTTAGG | 4543–4519 | 4534–4510 | 4358–4334 | 4364–4340 | 4330–4306 |
| PROBE6: | 18 | CTACTATATTGTTACCACACAGCAA | 4135–4159 | | | | |
| PROBE11: | 19 | ATTGTGCAAACGCAACAATAATGGT | | 4126–4150 | | | |
| PROBE16: | 20 | ATGACAAATCTTGATACTGCATCCA | | | 3849–3873 | | |
| PROBE18: | 21 | AATATTGGTGGGATACATGACAATG | | | | 3887–3911 | |
| PROBE33: | 22 | ACAGCATATGACACAACAAGAGTAA | | | | | 4057–4081 |

TABLE 4

SEQUENCES WHICH CAN BE USED: 1) TOGETHER AS GENERAL PROBES OR PCR PRIMERS, AND 2) AS TYPE-SPECIFIC PROBES
SET "c"

| PROBE | SEQ ID No. | SEQUENCE | MAP POSITION: | | | | |
|---|---|---|---|---|---|---|---|
| | | | TYPE 6 | TYPE 11 | TYPE 16 | TYPE 18 | TYPE 33 |
| A-PCR10: | 23 | TTTATGGATATTATTGGTTTACATAG | 5248–5273 | 5239–5264 | 5081–5106 | 5065–5090 | 5050–5075 |
| B-PCR11 | 24 | TCTGAAAAAAAATAGGGAATACGTTT | 5789–5764 | 5771–5746 | 5637–5612 | 5613–5588 | 5594–5569 |
| PROBE6: | 25 | CCCTGTTACAAATATATCAGATACA | 5508–5532 | | | | |
| PPOBE11: | 26 | TTCTGTTACACAGTCTTATCTTACC | | 5499–5524 | | | |
| PROBE16: | 27 | CCATCTGTACCCTCTACATCTTTAT | | | 5381–5405 | | |
| PROBE18: | 28 | CCTTTGCATTTTTTAAATATTCGCC | | | | 5346–5370 | |
| PROBE33: | 29 | ATAATGTACACACCCCAATGCAACA | | | | | 5321–5345 |

TABLE 5

SEQUENCES WHICH CAN BE USED: 1) TOGETHER AS GENERAL PROBES OR PCR PRIMERS,
AND 2) AS TYPE-SPECIFIC PROBES
SET "d"

| PROBE | SEQ ID No. | SEQUENCE | MAP POSITION: TYPE 6 | TYPE 11 | TYPE 16 | TYPE 18 | TYPE 33 |
|---|---|---|---|---|---|---|---|
| A-PCR12 | 30 | AGGGCTGGTACTGTGGGGGAAACTGT | 6563–6588 | 6548–6573 | 6423–6448 | 6399–6424 | 6380–6405 |
| B-PCR13: | 31 | GCTTTTTGTAGCCAATATGGTTTATT | 6723–6698 | 6708–6683 | 6583–6558 | 6559–6534 | 6540–6515 |
| PROBE6: | 32 | AATTAAGGGTAGTGGAAATCGCACG | 6604–6628 | | | | |
| PROBE11: | 33 | GGTAAAAGGGGGTAATAACAGATCA | | 6589–6613 | | | |
| PROBE16: | 34 | GTCTACTGCAAATTTAGCCAGTTCA | | | 6479–6503 | | |
| PROBE18: | 35 | TATGCCTGCTTCACCTGGCAGCTGT | | | | 6455–6479 | |
| PROBE33: | 36 | ACTACTGCCTCTATTCAAAGCAGTG | | | | | 6437–6461 |

EXAMPLE 5

Sequences were selected according to an unique algorithm developed to chose consensus sequences. The following sequences are consensus sequences so selected which should each hybridize with each of human papilloma virus types 6, 11, 16, 18 and 33. These sequences should hybridize in unique positions, the map positions of which are listed in Tables 6 and 7.

TABLE 6

PROBE SEQUENCES

| PROBE | SEQUENCE* | | | | | | SEQ ID No. |
|---|---|---|---|---|---|---|---|
| 1 | AATTAGNGAA | TATAGACATT | | | | | 37 |
| 3 | TATGGCTATT | CTGAAGTGGA | AGCTGNNNNN | CNACAGAT | | | 38 |
| 4 | TTAGTTAGAC | CATTTAAAAG | TGATAAAACA | ACNTGTNCAG | ATTGG | | 39 |
| 6 | TGGATANAAA | GACAAACNGT | TATACAACAT | AGTTTNGATG | AT | | 40 |
| 11 | TGGATAAAAT | ATAGATGTNC | TAAAATAGAT | GATGGAGGAA | ATTGGA | | 41 |
| 12 | CATTTTTAAG | TGCATTAAAA | TTATTTTTGC | AAGGNACNCC | NAAAAAAAA | | 42 |
| 15 | GTTGGACATA | TATNGATACN | TATATGAGAA | ATGCGTTAGA | TGG | | 43 |
| 18 | TCAAAGACTA | AAGCACATAA | AGCNATTGAA | CTGCAAATGG | | | 44 |
| 20 | CATTTAAAAG | GTGANTCNAA | TAGTTTAAAA | TGTTTAAGAT | ATAGCAGATT | | 45 |
| 22 | TCTATTGTGT | CNTTAATNGA | AGAATCTAGT | NTTATTAATG | CAGGTGCACC | | 46 |
| 24 | TACATAGGCC | TGCTATAACN | TCCAGNCGTG | GTNNTGTGCG | NTTAGTAGA | | 47 |
| 25 | CGTAAACGTN | TTCCCTATTT | TTTTNCAGAT | GTCTNTGTGG | CGGCCTAGTG | A | 48 |
| 26 | GTTGTNANCA | CGGATGANTA | TGTTACTCGC | ACAA | | | 49 |
| 27 | GTTGGACATC | CATATTTT | | | | | 50 |
| 28 | CAATATAGGG | TATTTAGGGT | NCNGTTACC | | | | 51 |
| 30 | AATAAATTTG | GATTNCCTGA | CACCTCNNTT | TATAAT | | | 52 |
| 36 | GATGGTGATA | TGGTTGATAC | AGGCTTTGGT | GCTATGGA | | | 53 |
| 37 | CATTNCANGC | NAATAAANGT | GATGTTCCTN | TNGATATTTG | T | | 54 |
| 38 | AAATATCCAG | ATTATTTANA | AATGG | | | | 55 |
| 39 | GTTACNTCTG | ANGCNCAATT | ATTTAATAAAC | CATATTGGCT | ACAANNNGCA | CA | 56 |
| 41 | AATGGTATTT | GTTGGGGTAA | TCAATTATTT | GTTACTGTGG | TAGATACC | | 57 |
| 46 | TTTTGGGAGG | TTAATTTAAA | NGAAAAGTTT | TCTGCAGANT | TAGATCA | | 58 |

*N = Unspecified nucleotide

TABLE 7

PROBE HOMOLOGY FOR HPV TYPES 6, 11, 16, 18, 33

| PROBE | SEQ ID No. | MAP POSITION: TYPE 6 | TYPE 11 | TYPE 16 | TYPE 18 | TYPE 33 |
|---|---|---|---|---|---|---|
| 1 | 37 | 320–339 | 320–339 | 319–338 | 326–345 | 324–343 |
| 3 | 38 | 1240–1271 | 1240–1271 | 1263–1294 | 1322–1353 | 1275–1306 |
| 4 | 39 | 1498–1542 | 1498–1542 | 1527–1571 | 1598–1642 | 1521–1567 |
| 6 | 40 | 1849–1890 | 1849–1890 | 1878–1919 | 1949–1990 | 1872–1913 |
| 11 | 41 | 2107–2153 | 2107–2153 | 2136–2182 | 2207–2253 | 2130–2176 |
| 12 | 42 | 2198–2246 | 2198–2246 | 2227–2275 | 2298–2346 | 2121–2269 |
| 15 | 43 | 2417–2459 | 2417–2459 | 2446–2488 | 2517–2559 | 2440–2482 |
| 18 | 44 | 2915–2954 | 2915–2954 | 2947–2986 | 3021–3060 | 2941–2980 |
| 20 | 45 | 3587–3636 | 3584–3633 | 3622–3668 | 3687–3733 | 3580–3626 |
| 22 | 46 | 4729–4778 | 4720–4769 | 4544–4593 | 4547–4596 | 4516–4565 |
| 24 | 47 | 5267–5317 | 5258–5308 | 5100–5150 | 5088–5138 | 5069–5119 |

TABLE 7-continued

PROBE HOMOLOGY FOR HPV TYPES 6, 11, 16, 18, 33

| PROBE | SEQ ID No. | MAP POSITION: TYPE 6 | TYPE 11 | TYPE 16 | TYPE 18 | TYPE 33 |
|---|---|---|---|---|---|---|
| 25 | 48 | 5761–5806 | 5743–5788 | 5609–5660 | 5585–5636 | 5566–5617 |
| 26 | 49 | 5846–5880 | 5828–5862 | 5697–5731 | 5673–5707 | 5654–5688 |
| 27 | 50 | 5918–5935 | 5900–5917 | 5769–5786 | 5745–5762 | 5726–5743 |
| 28 | 51 | 5984–6012 | 5966–5994 | 5841–5869 | 5817–5835 | 5801–5819 |
| 30 | 52 | 6020–6055 | 6002–6037 | 5877–5912 | 5853–5888 | 5837–5872 |
| 36 | 53 | 6365–6402 | 6350–6387 | 6225–6262 | 6201–6238 | 6182–6219 |
| 37 | 54 | 6410–6451 | 6395–6436 | 6270–6311 | 6246–6287 | 6227–6268 |
| 38 | 55 | 6464–6488 | 6449–6473 | 6324–6348 | 6300–6324 | 6281–6305 |
| 39 | 56 | 6674–6726 | 6659–6711 | 6534–6586 | 6510–6562 | 6491–6543 |
| 41 | 57 | 6737–6784 | 6722–6769 | 6597–6644 | 6573–6620 | 6554–6601 |
| 46 | 58 | 7109–7155 | 7094–7140 | 6972–7018 | 6951–6997 | 6926–6972 |

EXAMPLE 6

The following reagents were mixed in a 0.5 mL polypropylene tube as follows for the Ligase Chain Reaction (LCR):

| Reagent | Volume | Final Concentration |
|---|---|---|
| Water | 21 μL | |
| Reaction Buffer | 10 μL | 50 mM EPPS pH 7.8 |
| | | 10 mM NH$_4$Cl |
| | | 10 mM MgCl$_2$ |
| | | 100 mM K$^+$ (from all sources) |
| | | 0.001% BSA |
| | | 1 mM DDT |
| Nicotine Adenine Dinucleotide (NAD) | 0.5 μL | 100 μL |
| ProbeA (sense) | 4 μL | 5.0 × 10$^{11}$ molecules |
| ProbeA' (antisense, 5'-phosphate) | 4 μL | 7.5 × 10$^{11}$ molecules |
| ProbeB (sense, 5'-phosphate) | 4 μL | 7.5 × 10$^{11}$ molecules |
| Probe B' (antisense) | 4 μL | 5.0 × 10$^{11}$ molecules |
| Target (including human placental carrier DNA at 10 μg/mL) | 1.5 μL | 15 ng/50 μL |
| DNA ligase, Thermus thermophilus | 1 μL | |

This reaction mixture was overlayed with 30 μL of mineral oil. The tube was placed in an instrument capable of incubation at several temperatures (e.g. thermal cycler from Coy Laboratory Products (Ann Arbor, Mich.) or the Programmable Cycler Reactor™ (available from Ericomp, San Diego, Calif.), and then subjected to several cycles of programmed temperature change. Each cycle involved incubation at 50° C. for one minute and 85° C. for one minute.

EXAMPLE 7

The following procedure was used when performing the Ligase Chain Reaction (LCR), which is described in published European Patent Application No. 0 320 308 A2. The reagents of Example 6 were utilized in the procedure as follows: Two probes (A and B) complementary to immediately adjacent to regions of a target sequence were hybridized and ligated. This ligated probe was denatured away from the target, and hybridized with two additional probes (A' and B') of sense opposite to the initial probes (A and B). The secondary probes then were ligated. Subsequent cycles of denaturation/hybridization/ligation created the formation of double-length probes of both + and − sense.

EXAMPLE 8

The following sequences were found to amplify a section of the L1 region of HPV type 16 by following the procedures of Examples 6 and 7.

| PROBE | SEQ ID No. | SEQUENCE | | | MAPS TO HPV16 AT: |
|---|---|---|---|---|---|
| LCR1A | 59 | AAGTTGTAAG | CACGGATGAA | TATGT | 5695–5719 |
| LCR1A' | 60 | pACATATTCAT | CCGTGCTTAC | AACT | 5719–5696 |
| LCR1B | 61 | pTGCACGCACA | AACATATATT | ATCA | 5720–5743 |
| LCR1B' | 62 | ATGATAATAT | ATGTTTGTGC | GTGCA | 5744–5720 |

EXAMPLE 9

A linearized plasmid which contained a full-length papilloma virus type 16 insert (p65.16.8; HPV16) was used as the target. LCR1 (Example 8) contained $^{32}$P-phosphate at the 5' end. The thermal cycler employed, which was capable of incubation at several temperatures, was obtained from Coy Laboratory Products (Ann Arbor, Mich.). Following cycles of LCR as described in Examples 6 and 7, 10 μL aliquots were analyzed by electrophoresis through 4% agarose (5:3 ratio of NuSieve®:SeaKem® GTG, available from the FMC Corp., Rockland, Me.) in 0.089 M TRIS, 0.089 M borate and 2 mM EDTA. The dried gel then was exposed to film.

Figure 4:
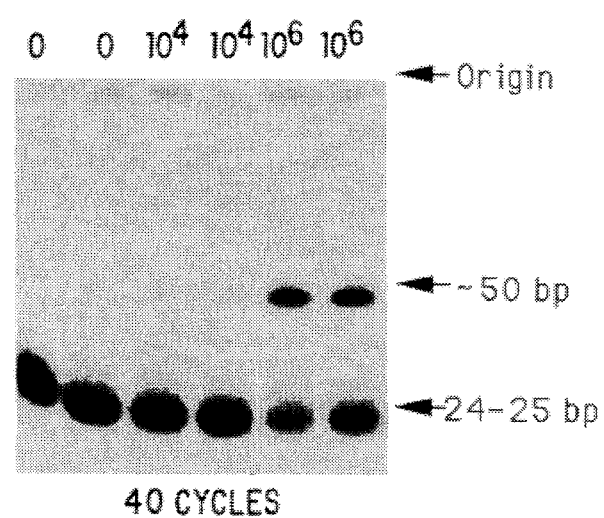
FIG. 4 is a photograph of an autoradiogram showing the results when LCR1A, LCR1A', LCRB AND LCRB' were used to amplify plasmid p65.16.8 at two different concentrations of plasmid.

FIG. 4 is a photograph of the autoradiogram. Lanes 1,2 show LCR in the absence of HPV16 target. Lanes 3,4 show LCR in the presence of $10^4$ molecules p65.16.8. Lanes 5,6 show LCR in the presence of $10^6$ molecules p65.16.8. All lanes show the presence of a band at about 24–25 bp, corresponding to unligated probes. It is observable that lanes 1 through 4 show very little band at about 50 bp, corresponding to the ligated LCR probe, whereas lanes 5 and 6 show an intense band at this size.

EXAMPLE 10

The target, cycler and sequences were the same as in Examples 8 and 9. Some of the oligonucleotides used as probes had chemical labels covalently attached at the ends distal from ligation. These labels were: 5'-fluorescein-LCR1A, 3'-fluorescein-LCR1A', 3'-biotin-LCR1B and 5'-biotin-LCR1B'. Covalent attachment was performed by standard methods, that is, by reaction of amine-terminated oligos with FITC or biotin-NHS-ester essentially following the procedures described in Kansal et al., *Tet. Letters* 29:5537–5540 (1988).

Following LCR as described above in Examples 6 and 7, the mixtures were analyzed using the immunochromatography detection system described in published European Patent Application No. 0262328. Briefly, this invlves the preparation of two immunochromatography reagents: antibody-coated colloid and antibody-treated nitrocellulose.

The colloid was polypyrrole, prepared by diluting polypyrrole to 0.05% solids in MES buffer, pH 6.0, containing 120 μg anti-biotin antibody in a total volume of 500 μL. The mixture was allowed to incubate 20 minutes at 55° C. with brief vortex mixing every 5 minutes. After this incubation, 10 μL @1% TWEEN-20 and 25 μL @10% ovalbumin in 25 mM BIS-TRIS, pH 6.5, were added. The mixture was sonicated briefly, and washed by centrifugation.

The nitrocellulose strip was 5 μm pore size, to which anti-fluorescein was added in a thin line by capillary whip.

By virtue of its double-labeled nature (fluorescein and biotin), the ligated LCR product linked antibiotin-conjugated polypyrrole particles to the antifluorescein-conjugated nitrocellulose. Unligated LCR probes are singly-labeled, and did not form this link. A 25 μL aliquot of the LCR mixture was added to 100 μL of a buffer comprising 100 mM TRIS at pH 8.0, 150 mM NaCl, and 2% BSA. A 10 μL aliquot of polypyrrole was added. Next, a 7×0.3 cm strip of nitrocellulose, with antifluorescein adsorbed at a spot 1.5 cm from the lower end, was dipped into the suspension. The suspension was allowed to rise up the nitrocellulose strip by capillary action until the solvent front reached within 1 cm of the top of the strip. A positive reaction was indicated by the presence of a solid black line at the locus of the antifluorescein on the strip.

Figure 5:
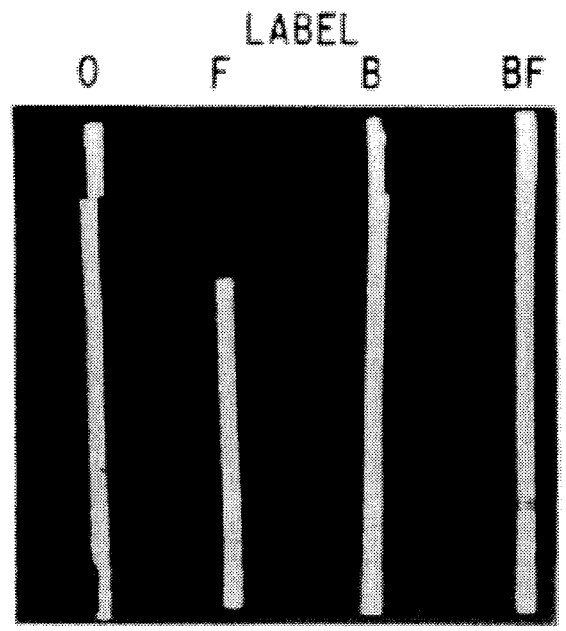
FIG. 5 is a photograph of nitrocellulose strips wherein LCR primers LCR1A, LCR1A', LCRB and LCRB' are utilized in conjunction with fluorescein, biotin or no signal generating compound.

FIG. 5 is a photograph of the resulting nitrocellulose strips. Referring to FIG. 4, "O" represents all probes without chemical labels attached to them; "F" shows fluorescein-LCR1A and fluorescein LCR1A', with no label on LCR1B or LCR1B'; "B" shows biotin-LCR1B and LCR1B', with no label on LCR1A or LCR1A'; "BF" shows fluorescein-LCR1A, fluorescein-LCR1A', biotin-LCR1B, and LCR1B'. It should be noted that only in the case BF does polypyrrole complex at the locus of antifluorescein on the nitrocellulose strip.

EXAMPLE 11

The following sequences were determined to be specific for HPV types 11, 16 and 18, as indicated in Table 8.

TABLE 8

| Probe | SEQ ID No. | Sequence | | | |
|---|---|---|---|---|---|
| HPV11: | | | | | Maps to HPV11 at: |
| LCR2A | 63 | ACCTGTTGGT | AAAAGGGGGT | AATAA | 6582–6607 |
| LCR2A' | 64 | pTTATTACCCC | CTTTTACCAA | CAGG | 6607–6583 |
| LCR2B | 65 | pCAGATCATCT | GTAGCTAGTA | GTAT | 6608–6630 |
| LCR2B' | 66 | ATACTACTAG | CTACAGATGA | TCTG | 6631–6608 |
| HPV16: | | | | | Maps to HPV16 at: |
| LCR3A | 67 | ATTTATACAT | TAAAGGCTCT | GGGTC | 6457–6482 |
| LCR3A' | 68 | pGACCCAGAGC | CTTTAATGTA | TAAA | 6482–6458 |
| LCR3B | 69 | pTACTGCAAAT | TTAGCCAGTT | CAAA | 6483–6505 |
| LCR3B' | 70 | ATTTGAACTG | GCTAAATTTG | CAGTA | 6506–6483 |
| HPV18: | | | | | Maps to HPV18 at: |
| LCR4A | 71 | CCTTATATAT | TAAAGGCACA | GGTAT | 6433–6458 |
| LCR4A' | 72 | pATACCTGTGC | CTTTAATATA | TAAG | 6458–6434 |
| LCR4B | 73 | pGCCTGCTTCA | CCTGGCAGCT | GTGT | 6459–6481 |
| LCR4B' | 74 | CACACAGCTG | CCAGGTGAAG | CAGGC | 6482–6459 |

EXAMPLE 12

Linearized plasmids containing full-length papilloma virus inserts in pGEM3 were used as targets, as described in Example 3. These plasmids were pSP65.11.5 (HPV11), pSP65.16.8 (HPV16) and p63HPV18H(−) (HPV18). The probes of Example 11 were labeled with biotin as described in Example 9. The thermal cycler was from Coy Laboratory Products.

Following LCR as described above in Examples 6 and 7, reaction mixtures were analyzed by a reverse-blot procedure, as follows. Oligonucleotides specific for a particular HPV type were covalently attached to a cellulose membrane (Memtek™, Bellerica, Mass.). These sequences were obtained by coupling the interior "half" portions of the type specific LCR probes LCR2, LCR3 and LCR4, as shown in Table 9:

TABLE 9

TYPE SPECIFIC HPV PROBES and THEIR LCR PROBE ORIGINS

| TYPE | SEQ ID No. | SEQUENCE | LCR PROBE ORIGIN |
|---|---|---|---|
| 11 | 75 | AGGGGGTAAT AACAGATCAT CTGT | 3' half of LCR2A and 5' half of LCR2B |
| 11 | 76 | ACAGATGATC TGTTATTACC CCCT | 3' half of LCR2B' and 5' half of LCR2A' |
| 16 | 77 | AGGCTCTGGG TCTACTGCAA ATTT | 3' half of LCR3A and 5' half of LCR3B |
| 16 | 78 | AAATTTGCAG TAGACCCAGA GCCT | 3' half of LCR3B' and 5' half of LCR3A' |
| 18 | 79 | AGGCACAGGT ATGCCTGCTT CACC | 3' half of LCR4A and 5' half of LCR4B |
| 18 | 80 | GGTGAAGCAG GCATACCTGT GCCT | 3' half of LCR4B' and 5' half of LCR4A' |

The hybridization scheme was as follows:

The membrane was prehybridized for 15 minutes at 37° C. in hybridization buffer (0.75M NaCl, 0.075 M Sodium Citrate pH 7.0, 0.5% Bovine Serum Albumin [BSA], 0.5% polyvinylpyrolidine, 1.0% sodium dodecyl sulfate [SDS], and 0.1% herring sperm DNA). The samples were boiled for about 5 minutes. Then, 25 μL aliquots of boiled sample were placed into 1 mL of fresh hybridization buffer. This mixture was incubated with membrane for about 20 hours at 37° C. The membranes then were incubated with a 1:1000 dilution of streptavidin-alkaline phosphatase conjugate (available from BRL, Gaithersburg, Md.) in fresh hybridization buffer for 45 minutes at 37° C. Then, the membrane was washed at room temperature as follows: twice in SSC buffer (150 mM NaCl, 15 mM Sodium Citrate, pH 7.0) with 1% SDS, and twice in SSC buffer which additionally contained 1% Triton X-100® (available from Sigma Chem. Co., St. Louis, Mo.). The membrane was washed twice at 37° C. in SSC buffer containing 1% Triton X-100®, and twice again at room temperature in SSC buffer.

The membranes were incubated with approx. 1 mL of a 1:5 dilution of TestPack™ substrate (Strep A Testpack™ reagent C, list 1301G, available from Abbott Laboratories, Abbott Park, Ill.) in approximately 2 mL diluent obtained from Molecular Biosystems (lot WFP-0188, San Diego, Calif.). A blue color indicated a positive reaction.

Figure 6:
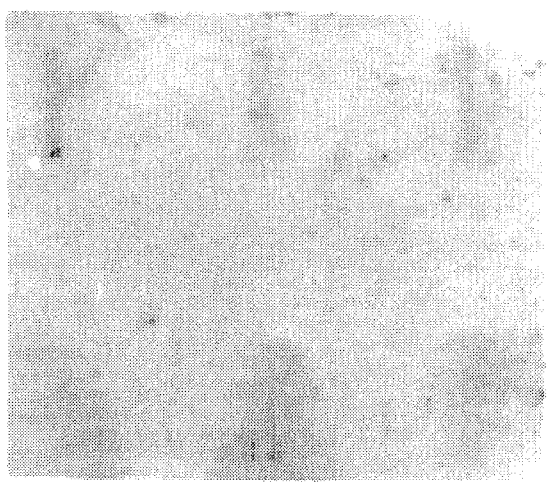
FIG. 6 is a photograph showing the amount of LCR product obtained from the reaction of LCR21, LCR2A', LCR2B and LCR2B' with pSP65.11.5.
Figure 7:
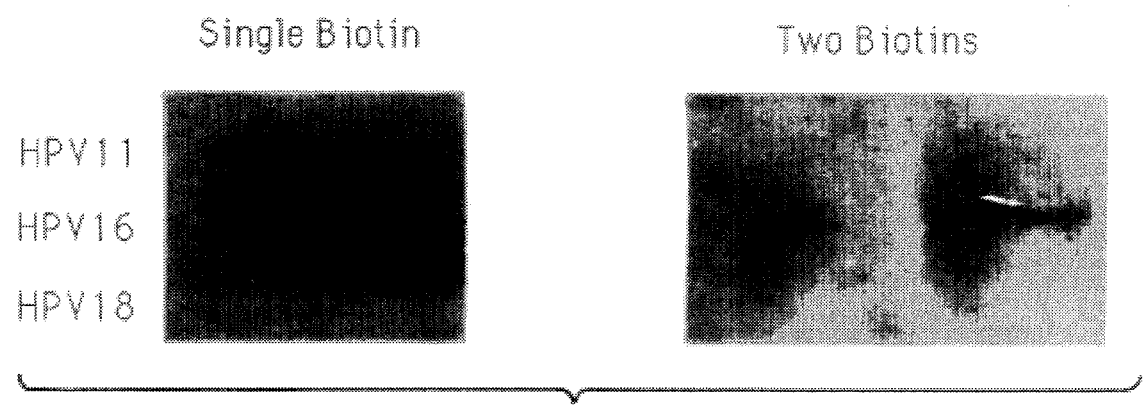
FIG. 7 is a photograph showing the amount of LCR product obtained from the reaction of LCR3A, LCR3A', LCR3B and LCR3B' with pSP16.8.
Figure 8:
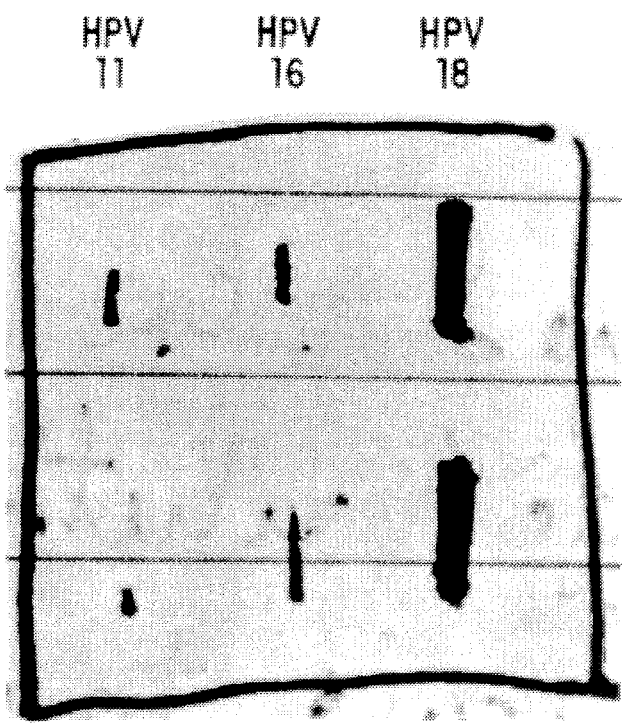
FIG. 8 is a photograph showing the amount of LCR product obtained from the reaction of LCR4A, LCR4A', LCR4B and LCR4B' with pG3G3HPV18H(−).

The results are shown in FIGS. 6–8. Referring to FIG. 6, the photograph shows the amount of LCR product from the reaction of LCR2A, LCR2A', LCR2B, and LCR2B' with pSP65.11.5. All six capture oligonucleotides were present on the membrane. A majority of the reaction product appears at the locus pf HPV11-specific oligos. Referring to FIG. 7, the photograph shows the amount of LCR product from the reaction of LCR3A, LCR3A', LCR3B and LCR3B' with pSP65.16.8. All six capture oligonucleotides were present on the membrane. All reaction product appears at the locus of HPV16-specific oligonucleotides. Referring to FIG. 8, the sketch indicates the amount of LCR product from the reaction of LCR4A, LCR4A', LCR4B AND LCR4B' with pG3G3HPV18H (–). All six capture oligonucleotides were present on the membrane. Virtually all reaction product appears at the locus of HPV18-specific oligos.

EXAMPLE 13

The following sequences were determined to be specific for a portion of the E6 region of HPV type 16:

| Probe | SEQ ID No. | Sequence | | | Maps to: |
|---|---|---|---|---|---|
| LCR5A | 81 | GCTGCAAACA | ACTATACATG | ATATAA | 157–182 |
| LCR5A' | 82 | pTTATATCATG | TATAGTTGTT | TGCAGC | 182–157 |
| LCR5B | 83 | pTATTAGAATG | TGTGTACTGC | AAGCA | 183–208 |
| LCR5B' | 84 | TGCTTGCAGT | ACACACATTC | TAATA | 208–157 |

EXAMPLE 14

Base-denatured plasmids which contained full-length papilloma virus inserts in pGEM3 were used as targets. These plasmids were pG3HPV6(+) (HPV6), pSP65.11.5 (HPV11), pSP65.16.8 (HPV16), p63HPV18H(–) (HPV18), p63:HPV31 (HPV31), pLNK322:HPV33 (HPV33), pBR322:HPV35 (HPV35), pUC19:HPV52 (HPV52), pLNK322:HPV58 (HPV58), pUC9:HPV59 (HPV59) and PBR322:HPV61 (HPV61). All of the oligonucleotides used as probes from Example 13 had chemical labels covalently attached at the ends distal from ligation. These labels were: 5'-fluorescein-LCR5A, 3'-fluorescein-LCR5A', 3'-biotin-LCR5B and 5'-biotin-LCR5B'. Covalent attachment was performed by known methods, i.e., reaction of amine-terminated oligonucleotides with FITC or biotin-NHS-ester essentially following the procedures of Kansal et al., Tet. Letters 29:5537–5540 (1988). The thermal cycler used was obtained from Coy Laboratory Products, Ann Arbor, Mich.

Following the LCR procedure of Examples 6 and 7, the mixtures were analyzed using a prototype version of the $IM_x$® instrument (Abbott Laboratories, Abbott Park, Ill.), following the protocol for microparticle enzyme immunoassays as follows. A 40 μL aliquot of an LCR mixture was diluted 1:1 with distilled water. This diluted mixture was incubated with 50 μL antifluorescein-conjugated polystyrene microparticles for five (5) minutes to form a suspension of immune complexes on the microparticles. This suspension then was transferred to an inert glass fiber matrix, to which the microparticles became attached. The matrix was washed with buffer (0.3M NaCl, 10 mM TRIS pH8, 0.1%$NAN_3$). Any immune complexes attached to the glass matrix was detected by using alkaline phosphatase-labeled conjugate that catalyzed the hydrolysis of 4-methylumbelliferone. The rate at which the 4-methylumbelliferone was generated on the matrix was proportional to the concentration of LCR product formed in the reaction mixture.

Figure 9:
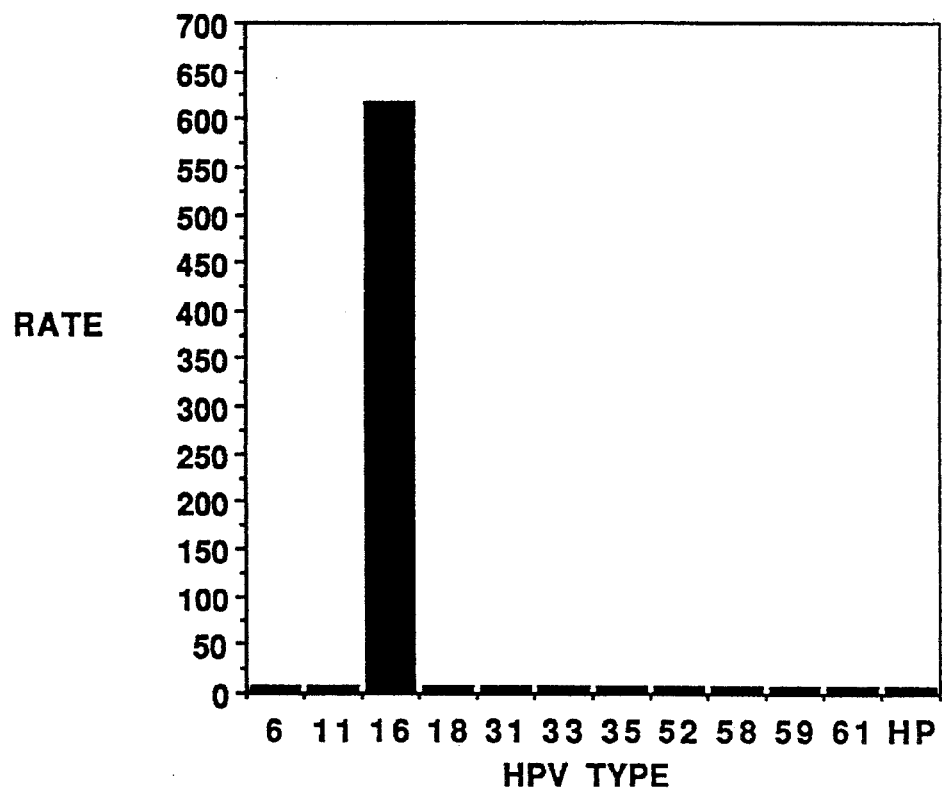
FIG. 9 is a graph of results obtained from performing LCR on $10^7$ molecules of the selected target using LCR5A, LCR5A', LCR5B and LCR5B'. The rate of reaction of 4-methyllumbelliferone is expressed as fluorescence counts/second/second and plotted against the target HPV type.

Referring to FIG. 9, the graph shows the results obtained from performing LCR on $10^7$ molecules of the targets in shown. The rate shown is the rate of generation of 4-methylumbelliferone, and is expresssed as fluorescence counts/second/second. Background signal is approximately 10 c/s/s, as shown by the amplification of human placental DNA. The only values above background are those for sample containing HPV16, and those values are about 60 times background signal.

EXAMPLE 15

The following sequences were determined to be specific for a portion of the E6 region of HPV type 18:

| Probe | SEQ ID No. | Sequence | | | Maps to: |
|-------|------------|----------|---|---|----------|
| LCR6A  | 85 | CTTCACTGCA  | AGACATACAA | ATAA | 172–195 |
| LCR6A' | 86 | pTTATTTCTAT | GTCTTGCAGT | GAA  | 195–173 |
| LCR6B  | 87 | pCCTGTGTATA | TTGCAAGACA | GTAT | 196–219 |
| LCR6B' | 88 | TACTGTCTTG  | CAATATACAC | AGG  | 218–196 |

EXAMPLE 16

Plasmids which contained full-length papilloma virus inserts in pGEM3 were used as targets. The plasmids used were those described in Example 14. All of the oligonucleotides used as probes obtained from Example 15 had chemical labels covalently attached at the ends distal from ligation. The thermal cycler was obtained from Coy Laboratory Products, Ann Arbor, Mich.

Following LCR procedure described in Examples 6 and 7, the mixtures were analyzed as described in Example 14 using the prototype version of the $IM_x$® instrument (Abbott Laboratories, Abbott Park, Ill.).

Figure 10:
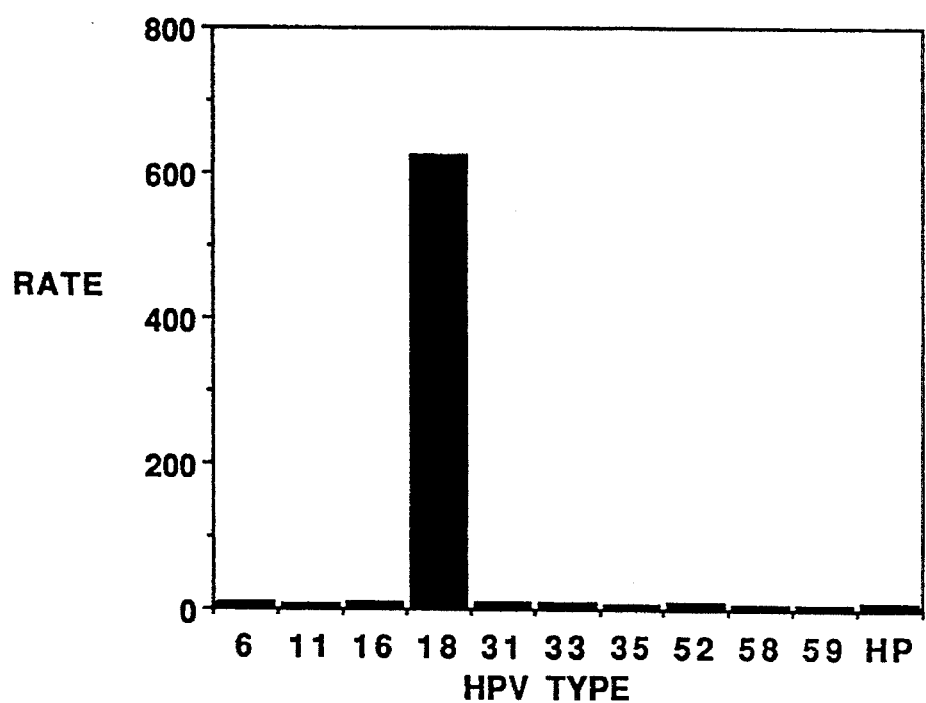
FIG. 10 is a graph of results obtained from performing LCR on $10^7$ molecules of the selected target using LCR6A, LCR6A', LCR6B and LCR6B'. The rate of reaction of 4-methyllumbelliferone is expressed as fluorescence counts/second/second and plotted against the target HPV type.

Referring to FIG. 10, the graph dislays the results obtained from performing LCR on $10^7$ molecules of the targets. The rate shown is the rate of generation of 4-methylumbelliferone, and is expressed as fluorescence counts/second/second. Background signal is approximately 15 c/s/s, as shown by the amplification of human placental DNA. The only values above background are those for sample containing HPV18, and those values are about 40 times background signal.

EXAMPLE 17

The following sequences were determined to be specific for a portion of the E6 region of HPV type 18:

| Probe | SEQ ID No. | Sequence | | | Maps to: |
|-------|------------|----------|---|---|----------|
| LCR7A  | 89 | TATATTGCAA  | GACAGTATTG | GAAC  | 200–223 |
| LCR7A' | 90 | pGTTCCAATAC | TGTCTTGCAA | TTTA  | 223–200 |
| LCR7B  | 91 | pTTACAGAGGT | ATTTGAATTT | GCATT | 224–249 |
| LCR7B' | 92 | AATGCAAATT  | CAAATACCTC | TGTAA | 249–224 |

EXAMPLE 18

Plasmids which contained full-length papilloma virus inserts in pGEM3 were used as targets. The plasmids were those of Example 14. All of the oligonucleotides from Example 17 which were used as probes had chemical labels covalently attached at the ends distal from ligation. The thermal cycler was as described in Example 16.

Following the LCR procedure of Examples 6 and 7, the mixtures were analyzed as described in Example 14 using the prototype version of the $IM_x$ instrument (Abbott Laboratories, Abbott Park, Ill.).

Figure 11:
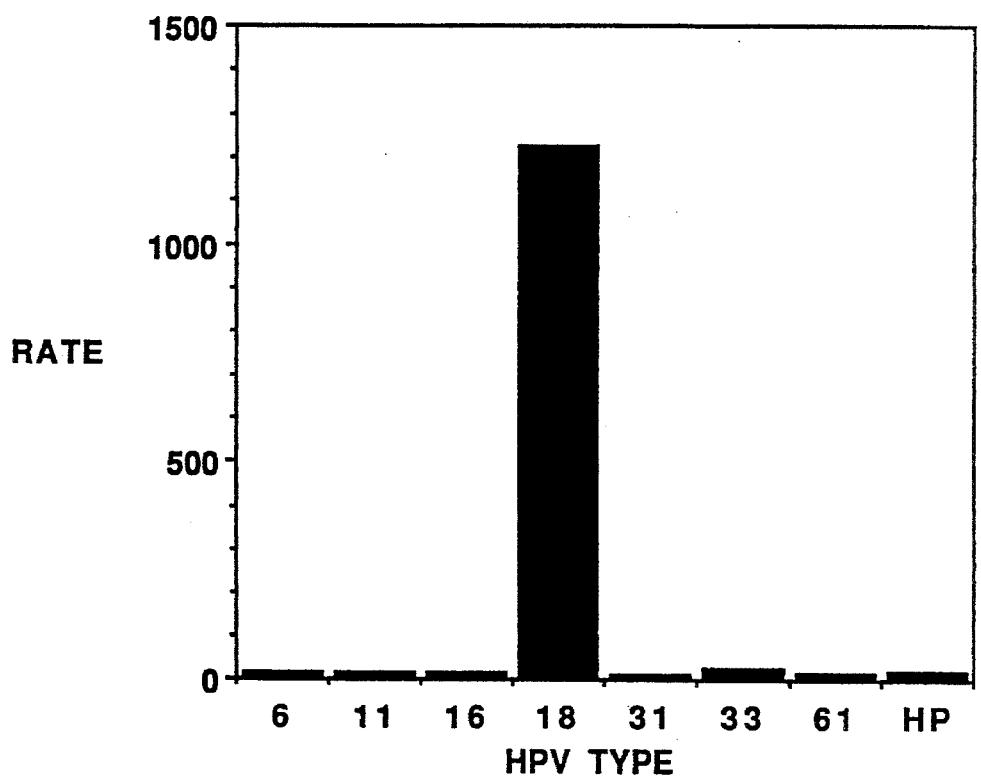
FIG. 11 is a graph of results obtained from perfomring LCR on $10^7$ molecules of the selected target using LCR7A, LCR7A', LCR7B and LCR7B'. The rate of reaction of 4-methyllumbelliferone is expressed as fluorescence counts/second/second and plotted against the target HPV type.

Referring to FIG. 11, the graph shows the results obtained from performing LCR on $10^7$ molecules of the targets. The rate shown is the rate of generation of 4-methylumbelliferone, and is expressed as fluorescence counts/second/second. Background signal is approximately 15 c/s/s, as shown by the amplification of human placental DNA. The only values above background are those for sample containing HPV18, and those values are about 80 times background signal.

EXAMPLE 19

The following sequences were determined to be specific for a portion of the E6 region of HPV type 16.

| Probe | SEQ ID No. | Sequence | | | Maps to: |
|-------|------------|----------|---|---|----------|
| LCR8A  | 93 | GTATGGAACA  | ACATTAGAAC | AGCA | 352–375 |
| LCR8A' | 94 | pTGCTGTTCTA | ATGTTGTTCC | ATAC | 375–352 |
| LCR8B  | 95 | pATACAACAAA | CCGTTGTGTG | ATTT | 376–399 |
| LCR8B' | 96 | AAATCACACA  | ACGGTTTGTT | GTAT | 399–376 |

EXAMPLE 20

Plasmids which contained full-length papilloma virus inserts in pGEM3 were used as targets. All of the oligonucleotides from Example 21 used as probes had chemical labels covalently attached at the ends distal from ligation. The thermal cycler was as described in Example 16.

Following LCR procedure of Examples 6 and 7, the mixtures were analyzed as described in Example 14 using the prototype version of the $IM_x$® instrument (Abbott Laboratories, Abbott Park, Ill.).

Figure 12:
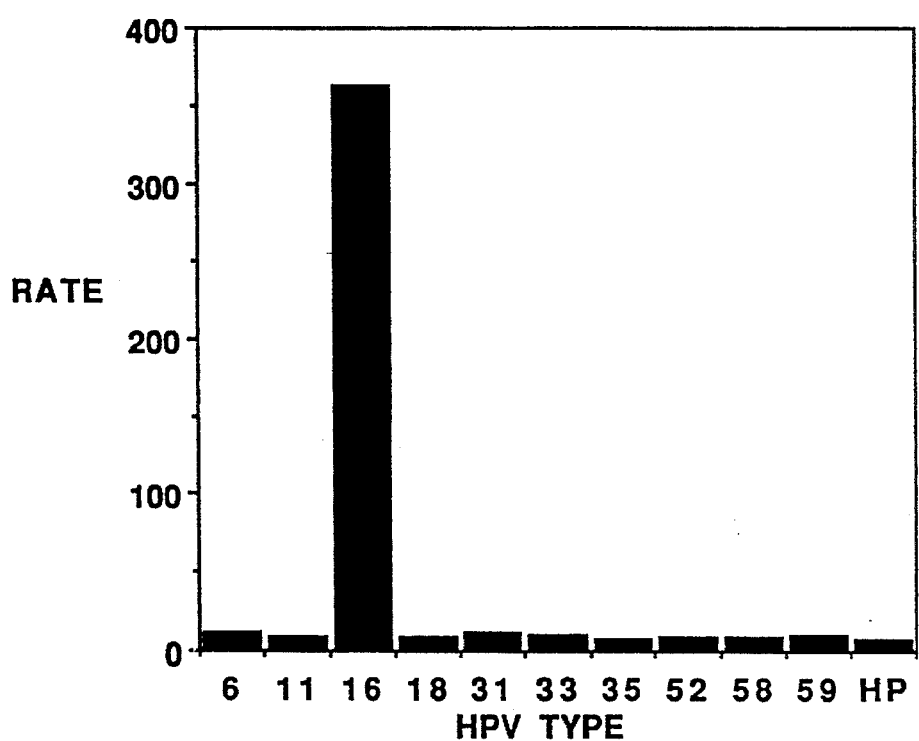
FIG. 12 is a graph of results obtained from perfomring LCR on $10^7$ molecules of the selected target using LCR8A, LCR8A', LCR8B and LCR8B'. The rate of reaction of 4-methyllumbelliferone is expressed as fluorescence counts/second/second and plotted against the target HPV type.

Referring to FIG. 12, the graph details the results obtained from performing LCR on $10^7$ molecules of the targets. The rate shown is the rate of generation of 4-methylumbelliferone, and is expressed as fluorescence counts/second/second. Background signal is approximately 10 c/s/s, as shown by the amplification of human placental DNA. The only values above background are those for sample containing HPV16, and those values are about 36 times background signal.

EXAMPLE 21

The attached Appendix (example 21) discloses the sequences of the invention aligned to known sequences.

We claim:

1. A type-specific oligonucleotide for determining the presence of human papilloma virus type 16, having a sequence selected from the group consisting of:

| SEQ ID No. | | | |
| --- | --- | --- | --- |
| 13 | AGGGCGCCAT | GAGACTGAAA | CAC, |
| 20 | ATGACAAATC | TTGATACTGC | ATCCA, |
| 27 | CCATCTGTAC | CCTCTACATC | TTTAT, |
| 34 | GTCTACTGCA | AATTTAGCCA | GTTCA, |
| 59 | AAGTTGTAAG | CACGGATGAA | TATGT, |
| 60 | ACATATTCAT | CCGTGCTTAC | AACT, |
| 61 | TGCACGCACA | AACATATATT | ATCA, |
| 62 | ATGATAATAT | ATGTTTGTGC | GTGCA, |
| 67 | ATTTATACAT | TAAAGGCTCT | GGGTC, |
| 68 | GACCCAGAGC | CTTTAATGTA | TAAA, |
| 69 | TACTGCAAAT | TTAGCCAGTT | CAAA, |
| 70 | ATTTGAACTG | GCTAAATTTG | CAGTA, |
| 77 | AGGCTCTGGG | TCTACTGCAA | ATTT, |
| 78 | AAATTTGCAG | TAGACCCAGA | GCCT, |
| 81 | GCTGCAAACA | ACTATACATG | ATATAA, |
| 82 | TTATATCATG | TATAGTTGTT | TGCAGC, |
| 83 | TATTAGAATG | TGTGTACTGC | AAGCA, |

-continued

| SEQ ID No. | | | |
| --- | --- | --- | --- |
| 84 | TGCTTGCAGT | ACACACATTC | TAATA, |
| 93 | GTATGGAACA | ACATTAGAAC | AGCA, |
| 94 | TGCTGTTCTA | ATGTTGTTCC | ATAC, |
| 95 | ATACAACAAA | CCGTTGTGTG | ATTT and |
| 96 | AAATCACACA | ACGGTTTGTT | GTAT; | and their complements.

2. A method for determining the presence of human papilloma virus type 16 in a test sample, comprising:

a. hybridizing DNA in the test sample with at least one oligonucleotide selected from the group of claim 1, said oligonucleotide being conjugated to a signal generating compound capable of producing a detectable signal; and b. determining the presence of human papilloma virus by detecting the signal generated.

* * * * *